US009108913B2

(12) United States Patent
Daute et al.

(10) Patent No.: US 9,108,913 B2
(45) Date of Patent: Aug. 18, 2015

(54) CATALYST SYSTEM FOR THE PREPARATION OF AN ESTER AND PROCESSES EMPLOYING THIS ESTER (75) Inventors: Peter Daute, Beverstedt (DE); Martin Schäfer, Stubben (DE); Thomas Schweichler, Loxstedt (DE)

(73) Assignee: Emery Oleochemicals GmbH (DE)

( * ) Notice: Subject to any disclaimer, the term of this patent is extended or adjusted under 35 U.S.C. 154(b) by 524 days.

(21) Appl. No.: 13/519,993

(22) PCT Filed: Dec. 30, 2010

(86) PCT No.: PCT/EP2010/007974
§ 371 (c)(1),
(2), (4) Date: Jan. 14, 2013

(87) PCT Pub. No.: WO2011/079952
PCT Pub. Date: Jul. 7, 2011

(65) Prior Publication Data
US 2013/0109763 A1    May 2, 2013

(30) Foreign Application Priority Data

Dec. 30, 2009  (DE) .................. 10 2009 060 813

(51) Int. Cl.
| C07C 67/08 | (2006.01) |
| B01J 8/20 | (2006.01) |
| B01J 8/18 | (2006.01) |
| B01J 8/38 | (2006.01) |
| A61K 8/37 | (2006.01) |
| B01J 19/00 | (2006.01) |
| C08K 5/101 | (2006.01) |
| C09D 7/12 | (2006.01) |
| C09K 8/035 | (2006.01) |
| C10M 129/70 | (2006.01) |

(52) U.S. Cl.
CPC . *C07C 67/08* (2013.01); *A61K 8/37* (2013.01); *B01J 8/1836* (2013.01); *B01J 8/20* (2013.01); *B01J 8/382* (2013.01); *B01J 19/0066* (2013.01); *C08K 5/101* (2013.01); *C09D 7/1233* (2013.01); *C09K 8/035* (2013.01); *C10M 129/70* (2013.01); *B01J 2208/0084* (2013.01); *B01J 2208/00176* (2013.01); *B01J 2208/00212* (2013.01); *B01J 2208/00247* (2013.01); *B01J 2208/00283* (2013.01); *B01J 2208/00867* (2013.01); *B01J 2208/025* (2013.01)

(58) Field of Classification Search
None
See application file for complete search history.

(56) References Cited

U.S. PATENT DOCUMENTS

| 3,167,531 | A | 1/1965 | Parker et al. |
| 5,049,697 | A | 9/1991 | Bohen et al. |
| 6,774,166 | B1 | 8/2004 | Eichenauer et al. |

OTHER PUBLICATIONS

International Search Authority, International Search Report in corresponding No. PCT/EP2010/007974, dated Jul. 25, 2011, 3 pages.
International Search Authority, Written Opinion in corresponding No. PCT/EP2010/007974, dated Jul. 25, 2011, 8 pages.

*Primary Examiner* — Yevegeny Valenrod
(74) *Attorney, Agent, or Firm* — Wood, Herron & Evans, LLP (57) ABSTRACT The present invention relates to a process for the preparation of an ester in a reactor, wherein at least one of at least two different catalysts is an electron donor and a further catalyst is a sulphur-containing proton donor; a device, a process for the preparation of a thermoplastic composition comprising the ester prepared according to the invention, a process for the production of a shaped article comprising the ester according to the invention or the thermoplastic composition according to the invention, a process for the production of a packed product, a process for the production of an at least partly coated object, and uses of the esters according to the invention as an additive in various compositions.

15 Claims, 1 Drawing Sheet

CATALYST SYSTEM FOR THE PREPARATION OF AN ESTER AND PROCESSES EMPLOYING THIS ESTER

This application is a U.S. National Phase of PCT/EP2010/007974 entitled "Catalyst System For The Preparation Of An Ester And Processes Employing This Ester" filed Dec. 30, 2010, which claims the benefit of DE Application Serial Number 10 2009 060 813.3 entitled "Catalyst System For The Preparation Of An Ester And Processes Employing This Ester" filed Dec. 30, 2009, the disclosures of which are hereby incorporated by reference herein.

The present invention relates to a process for the preparation of an ester in a reactor, a device, a process for the preparation of a thermoplastic composition comprising the ester prepared according to the invention, a process for the production of a shaped article comprising the ester according to the invention or the thermoplastic composition according to the invention, a process for the production of a packed product, a process for the production of an at least partly coated object, and uses of the esters according to the invention as an additive in various compositions.

Esters, in particular those based on aliphatic carboxylic acids and alcohols, are employed successfully in a large number of uses. In the awareness that raw materials from fossil deposits are becoming scarcer, new sources of raw materials are being sought. Oils from animal or plant renewable raw materials which are broken down to fatty acids e.g. by ozonolysis and refunctionalized or derivatized in further steps appear to be particularly promising.

Ester preparation is an industrially important derivatization, for which various processes are known. These can be categorized in various ways. One possibility is classification into low temperature and high temperature processes. In this context, generally, low temperature processes are often more gentle, i.e. generate fewer side reactions and decomposition or oxidation products, and high temperature processes are characterized by higher rates of reaction.

In conventional low temperature processes, as a general rule proton acids or sulphonic acid derivatives are added as catalysts. In the case of proton acids in particular, such as sulphuric acid or phosphoric acid, by-products, in particular unsaturated compounds, are formed in a considerable proportion. The unsaturated substances formed by this procedure are as a general rule coloured, or form coloured compounds with atmospheric oxygen in a short time. This is perceived as a reduction in the product quality of the ester prepared. The unsaturated contents moreover often have the effect of a deterioration in the stability and durability of products to which these esters are added as an additive. The aggressiveness of the acid catalysts at elevated temperature additionally is a burden on the production plants. A usually low rate of reaction is considered to be a further disadvantage of the low temperature processes.

In the high temperature processes, organometallic complexes of the transition metals Ti, Zr, Al, Sn are conventionally employed as catalysts. Because of the high reaction temperature, however, still more coloured by-products are formed, so that expensive working up and/or purification processes become necessary. Furthermore, the removal of the catalyst from the end product is expensive.

EP 0 342 357 A2 describes a device and a process for carrying out esterifications. In this, esters are prepared from alcohols and fatty acids in a production plant at 200 to 250° C., the reaction mixture being led continuously over a particularly hot reaction zone with a short contact time and the preparation being carried out over reaction times of up to 20 hours.

With respect to industrial esterification reactions, there is need for improvement in various aspects in order to meet the requirements and demands of the market. The known processes have at least one, as a rule several of the disadvantages outlined below:

coloured nature or inadequate colourlessness of the products
undesirable by-products,
inadequate stability
low efficiency, high energy consumption, high production costs,
low yield,
impurities, in particular traces of heavy metals,
long reaction times.

There is therefore the need for improvement in the known processes and possibly the provision of new processes in order to be able to provide esters in an improved quality.

There is furthermore the demand for more efficient production processes or devices which have a lower consumption of energy and resources with high conversions, yields and selectivities and render after-treatment steps superfluous.

The present invention was based on the object of at least partly overcoming the disadvantages emerging from the prior art.

In particular, the present invention was based on the object of providing a process and a device with the aid of which by-products which differ from esters and play a part in the increase in the colour shading of the esters can be reduced, and in this way expensive and time-consuming purification steps can be reduced or even avoided.

A further object of the present invention was to provide additives for the preparation of thermoplastic compositions which, in addition to being environment-friendly, are suitable for modifying the properties of the thermoplastic composition in the desired manner and at the same time for obtaining thermoplastic compositions which meet high requirements, such as in the foodstuffs industry or in medicine.

A contribution towards achieving at least one of the above-mentioned objects is made by the subject matter of the category-forming claims, the sub-claims dependent upon these representing further embodiments according to the invention.

The present invention provides a process for the preparation of an ester at least based on
a. at least one alcohol component,
b. at least one carboxylic acid component,
c. optionally further additives,
d. at least two different catalysts, and
e. max. 20 wt. % of a solvent
as process components, comprising, in a reactor, the process steps:
i. provision of the process components,
ii. reaction of the process components to give an ester A,
iii. optionally after-treatment of the ester A,
wherein at least in each case one of the at least two different catalysts is an electron donor and a further catalyst of the at least two different catalysts is a sulphur-containing proton donor.

According to the present invention it is preferred that the carboxylic acid component contains non-metal atoms chosen from the group of carbon (C), oxygen (O), Nitrogen (N) or hydrogen (H). It is further preferred that no other non-metal atoms are present in the carboxylic acid component.

In principle, any alcohol component with one or more hydroxyl groups which is known to the person skilled in the art and appears to be suitable for carrying out the process according to the invention is suitable as the alcohol component for carrying out the process according to the invention. The term "alcohol component" as used here includes the alcohol in its protonated form, the alcohol in its deprotonated form, in particular salts of the alcohol, and also mixtures of the alcohol in its protonated form and its deprotonated form or mixtures of the alcohol in its protonated form, its deprotonated form and one or more salts of the alcohol.

Alcohols with a number of hydroxyl groups in a range of from 1 to 9 are preferably chosen as the alcohol component with one or more hydroxyl groups. Particularly preferably, an alcohol component with one or more, for example from 2 to 8 and most preferably 3 to 6 hydroxyl groups is employed. The number of carbon atoms in the alcohol with one or more hydroxyl groups is preferably in a range of from 3 to 30, particularly preferably 3 to 18, furthermore preferably 3 to 10 and most preferably 3, 4, 6 or 8.

A technical grade alcohol can also be employed as the alcohol component. "Technical grade" in connection with a chemical substance or chemical composition means that the chemical substance or the chemical composition contains small amounts of impurities. In particular, the chemical substance or the chemical composition can contain impurities in a range of from 5 to 20 wt. %, preferably from 5 to 15 wt. %, more preferably from 5 to 10 wt. %, based on the total amount of the chemical substance or chemical composition. Particularly preferably, the chemical substance or the chemical composition contains from 1.5 to 5 wt. % of impurities. Impurities are understood as meaning all contents which differ from the chemical substance or the chemical composition. For example, technical grade ethanol can contain from 5 to 8 wt. % of impurities. This example cannot be generalized for all alcohols, rather the content of impurities with respect to the classification as "technical grade" is substance- or composition-related, or also depends on the preparation process. This classification according to the substance and the preparation process is familiar to the person skilled in the art.

It is likewise conceivable that it is not an individual alcohol or an individual technical grade alcohol which is employed as the alcohol component, but a mixture of several alcohols in the context of the abovementioned chemical composition. For example, several forms of the alcohol in accordance with that stated above can be employed as a mixture. Preferably, several alcohols characterized by at least one of the following features, such as different number of carbon atoms, different number of hydroxyl groups or different structure, or alcohols which differ simultaneously in two or more of the abovementioned features, such as can be obtained, for example, as technical grade products from large-scale industrial processes, are employed.

According to a preferred embodiment, monofunctional, difunctional, trifunctional, tetrafunctional or pentafunctional alcohols, or a mixture of two or more of these, are suitable as the alcohol component.

Alcohol components which are suitable in this connection are based, for example, on the following monofunctional alcohols: 1-propanol, 2-propanol, 1-butanol, 2-butanol, 2,2-dimethyl-1-propanol, 2-methyl-1-propanol, 2,2-dimethyl-1-propanol, 2-methyl-2-propanol, 2-methyl-1-butanol, 3-methyl-1-butanol, 2-methyl-2-butanol, 3-methyl-2-butanol, 1-pentanol, 2-pentanol, 3-pentanol, cyclopentanol, cyclopentenol, glycidol, tetrahydrofuryl alcohol, tetrahydro-2H-pyran-4-ol, 2-methyl-3-buten-2-ol, 3-methyl-2-buten-2-ol, 3-methyl-3-buten-2-ol, 1-cyclopropyl-ethanol, 1-penten-3-ol, 3-penten-2-ol, 4-penten-1-ol, 4-penten-2-ol, 3-pentyn-1-ol, 4-pentyn-1-ol, propargyl alcohol, allyl alcohol, hydroxyacetone, 2-methyl-3-butyn-2-ol, 1-hexanol, 2-hexanol, 3-hexanol, i-hexanol, 4-methyl-2-pentanol, 4-methyl-3-pentanol, 3-methyl-1-pentanol, 3-methyl-2-pentanol, cyclohexanol, 1-heptanol, 2-heptanol, 3-heptanol, 4-heptanol, i-heptanol, 5-methyl-2-hexanol, 5-methyl-3-hexanol, 5-methyl-4-hexanol, 4-methyl-1-hexanol, 4-methyl-2-hexanol, 4-methyl-3-hexanol, 3-methyl-1-hexanol, 3-methyl-2-hexanol, 1-octanol, 2-octanol, 3-octanol, 4-octanol, i-octanol, 2-ethylhexanol, 1-nonanol, 2-nonanol, 3-nonanol, 4-nonanol, 5-nonanol, i-nonanol, 1-decanol, 2-decanol, 3-decanol, 4-decanol, 5-decanol, 1-undecanol, 2-undecanol, i-undecanol, 1-dodecanol, 2-dodecanol, i-dodecanol, 1-tridecanol, 2-tridecanol, i-tridecanol, tetradecanol, hexadecanol, Guerbet alcohol, heptadecanol, 1-octadecanol, oleyl alcohol, eicosanol, behenyl alcohol, or two or more of these.

The following are suitable as the alcohol component based on difunctional alcohols: 1,2-ethanediol, 1,2-propanediol, 1,3-propanediol, dihydroxyacetone, 2-methyl-1,3-propanediol, 2-butyne-1,4-diol, 3-butene-1,2-diol, 2,3-butanediol, 1,4-butanediol, 1,3-butanediol, 1,2-butanediol, 2-butene-1,4-diol, 1,2-cyclopentanediol, 3-methyl-1,3-butanediol, 2,2-dimethyl-1,3-propanediol, 4-cyclopentene-1,3-diol, 1,2-cyclopentanediol, 2,2-dimethyl-1,3-propanediol, 1,2-pentanediol, 2,4-pentanediol, 1,5-pentanediol, 4-cyclopentene-1,3-diol, 2-methylene-1,3-propanediol, 2,3-dihydroxy-1,4-dioxane, 1,6-hexanediol, 2,5-hexanediol, 3,4-hexanediol, 1,2-hexanediol, 1,2-cyclohexanediol, 1,3-cyclohexanediol, 1,2-heptanediol, 1,7-heptanediol, 2,6-heptanediol, 3,4-heptanediol, 1,2-cycloheptanediol, 1,3-cycloheptanediol, 1,4-cycloheptanediol, 1,2-octanediol, 1,8-octanediol, 2,7-octanediol, 4,5-octanediol, 1,2-cyclooctanediol, 1,3-cyclooctanediol, 1,4-cyclooctanediol, 1,5-cyclooctanediol, 1,2-nonanediol, 1,9-nonanediol, 2-methyl-1,9-octanediol, 2,2-dimethyl-1,9-octanediol, or two or more of these.

The following are suitable as the alcohol component based on trifunctional alcohols: glycerol, 1,2,4-butanetriol, erythrose, threose, trimethylolethane, trimethylolpropane, 2-hydroxymethyl-1,3-propanediol or two or more of these.

The following are suitable as the alcohol component based on tetrafunctional alcohols: erythritol, threitol, pentaerythritol, arabinose, ribose, xylose, ribulose, xylulose, lyxose, ascorbic acid, gluconic acid γ-lactone, or two or more of these.

The following are suitable as the alcohol component based on pentafunctional and more highly functional alcohols: arabitol, adonitol, xylitol and dipentaerythritol.

According to a further preferred embodiment, the alcohol component is chosen from glycerol, glycerol dimer, glycerol trimer, glycerol tetramer, oligoglycerols, pentaerythritol, pentaerythritol dimer, pentaerythritol trimer, trimethylolpropane, bistrimethylolpropane, n-octanol, i-octanol, 2-ethylhexanol, i-tridecanol, n-butanol, i-butanol, n-propanol, i-propanol, 2,2-dimethylpropanol, 1-octadecanol, cetyl alcohol, stearyl alcohol, oleyl alcohol, ethylene glycol, diethylene glycol, butyl glycol, dibutyl glycol, tributyl glycol, 2-propylheptanol, polyethylene glycol or two or more of these.

In this connection, reaction products of these alcohol components with ethylene oxide and/or propylene oxide are furthermore suitable, in each case independently between 2 and 30 units particularly preferably 2, 3, 4, 5, 6, 7, 8, 9 or 10 units of ethylene oxide and/or propylene oxide having been reacted on at least one, preferably two or more, particularly preferably all of the hydroxyl groups of the alcohol component. The use of di-, tri- or tetrabutyl glycol is moreover conceivable.

According to a further preferred embodiment, the alcohol component contains less than 10 wt. %, preferably less than 5 wt. % of nitrogen-containing compounds, based on the total weight of the alcohol component, nitrogen-containing compounds being both nitrogen-containing alcohol components and other nitrogen-containing organic compounds. The alcohol component furthermore preferably does not contain nitrogen atoms (N).

According to a further preferred embodiment, the alcohol component contains less than 10 wt. %, preferably less than 5 wt. % of aromatic ring compounds, based on the total weight of the alcohol component, aromatic ring compounds being both alcohols containing aromatic rings and other aromatic ring compounds. The alcohol component furthermore preferably does not contain aromatic ring compounds.

According to a further preferred embodiment, the alcohol component contains as non-metal atoms only non-metal atoms chosen from the group consisting of carbon (C), oxygen (O), nitrogen (N) or hydrogen (H) or several of these, preferably consisting of carbon (C), oxygen (O) and hydrogen (H).

In principle all carboxylic acids known to the person skilled in the art can be employed as the carboxylic acid component for the preparation of the ester. The term "carboxylic acid component" as used herein includes the carboxylic acid in its protonated form, the carboxylic acid in its deprotonated form, and also salts of the carboxylic acid, and also mixtures of at least two of the above, or of the carboxylic acid in its protonated form, its deprotonated form and at least one or more salts of the carboxylic acid.

The term "carboxylic acid component" furthermore in principle includes all compounds which contain at least one carboxylic acid group. This term also includes compounds which, in addition to the at least one carboxylic acid group, contain other functional groups, such as ether groups.

According to the invention, suitable carboxylic acids are, in particular, those which are based on plant or animal oils or fats, e.g. tallow, such as, for example, beef tallow, kidney tallow or bovine kidney fat, lard, fish oil, neat's foot oil, seed oil, such as, for example, argan oil, apricot kernel oil (marillen kernel oil), cottonseed oil, borage oil (borage seed oil), thistle oil, groundnut oil, hazelnut oil, hemp oil, rose-hip kernel oil, elder seed oil, jojoba oil, currant seed oil, coconut oil/coconut fat, kukui oil, kiwi seed oil, pumpkin seed oil, linseed soil, cameline oil, macadamia oil, almond oil, poppy oil, evening primrose oil, palm oil, palm kernel oil, peach kernel oil, rape oil, rice oil, castor oil, sea buckthorn kernel oil, mustard oil, nutmeg flower oil, sesame oil, shea oil, shea butter, soya oil, sunflower oil, walnut oil, grape seed oil, wheat germ oil or cedar oil, fruit pulp fats, such as, for example, olive oil, palm oil, avocado oil or sea buckthorn oil, or also germ oils, such as, for example, rape germ oil, rice husk oil, wheat germ oil, maize germ oil, rice germ oil, soya germ oil or sunflower germ oil, or a mixture of two or more of these. The use of tallow, of rape oil and of coconut, canola, palm, soya or sunflower oil is most preferred.

A technical grade carboxylic acid can furthermore also be employed as the carboxylic acid component. It is likewise conceivable that it is not an individual carboxylic acid or an individual technical grade carboxylic acid which is employed as the carboxylic acid component, but a mixture of several carboxylic acids. For example, several forms of the carboxylic acid in accordance with that stated above can be employed as a mixture. Preferably, several carboxylic acids characterized by at least one of the following features, a different number of carbon atoms, a different number of carboxylic groups or a different structure, or carboxylic acids which differ simultaneously in several of the above-mentioned features, such as can be obtained, for example, as technical grade products from large-scale industrial processes, are employed. The substance-related amount of impurities in the technical grade is familiar to the person skilled in the art.

The use of mono-, di- or polycarboxylic acids is preferred according to the invention. Possible carboxylic acid components are, in particular, saturated or unsaturated carboxylic acids, acid chlorides of the carboxylic acids and acid anhydrides of the carboxylic acids having a number of carbon atoms in a range of from 6 to 26, particularly preferably in a range of from 8 to 24, still more preferably in a range of from 10 to 22, moreover preferably in a range of from 12 to 20 and most preferably in a range of from 14 to 18. The carboxylic acid components furthermore preferably have from 8 to 12 C atoms.

Carboxylic acid components which are suitable in this connection are, for example, derived from the following monocarboxylic acids: acetic acid, propionic acid, butyric acid, valeric acid, caproic acid, oenanthic acid, caprylic acid (octanoic acid), i-octanoic acid, pelargonic acid (nonanoic acid), capric acid (decanoic acid), lauric acid (dodecanoic acid), myristic acid, palmitic acid, margaric acid, stearic acid, arachic acid, behenic acid or also unsaturated carboxylic acids, such as e.g. acrylic acid, methacrylic acid, 3-butenoic acid, 4-pentenoic acid, 5-hexenoic acid, 6-heptenoic acid, 7-octenoic acid, 8-nonenoic acid, 9-decenoic acid, undecylenic acid, palmitoleic acid, oleic acid, elaidic acid, vaccenic acid, icosenic acid, ricinoleic acid, 12-hydroxystearic acid, cetoleic acid, erucic acid, and polyunsaturated carboxylic acids, for example linoleic acid, linolenic acid, arachidonic acid, timnodonic acid, clupanodonic acid or cervonic acid.

Suitable carboxylic acid components based on dicarboxylic acids are, for example, malonic acid, maleic acid, fumaric acid, succinic acid, glutaric acid, adipic acid, pimelic acid, suberic acid, azelaic acid, sebacic acid, tartaric acid, malic acid, α-ketoglutaric acid, oxaloacetic acid, o-phthalic acid, m-phthalic acid or p-phthalic acid. Examples of a suitable tricarboxylic acid are trimellitic acid or citric acid. The use of a mixture of at least two of the abovementioned carboxylic acid components is furthermore conceivable.

According to a further preferred embodiment, the carboxylic acid component comprises more than 5 carbon atoms. Carboxylic acid components, in particular those with unsaturated groups, above all if they are short-chain carboxylic acid components, sometimes contain polymerization inhibitors. A polymerization of such unsaturated groups during the preparation or during the further processing, or both, is intended to be avoided by this means. Nevertheless, a change in colour, such as deepenings in colour or lightening in colour, often occurs in time in carboxylic acid components with polymerization inhibitors, which is found to be a disadvantage in many uses of the esters according to the invention, such as in coatings or the production of shaped articles. According to a further preferred embodiment, the carboxylic acid component contains no polymerization inhibitors.

According to a preferred embodiment, the carboxylic acid component is chosen from octanoic acid, i-octanoic acid, nonanoic acid, i-nonanoic acid, 9-decenoic acid, decanoic acid, i-decanoic acid, sebacic acid, palmitic acid, stearic acid, oleic acid, azelaic acid, pelargonic acid, trimellitic acid, adipic acid, erucic acid, behenic acid, $HOOC-C_{36}H_{72}-COOH$, phthalic anhydride.

According to a further preferred embodiment, the carboxylic acid component contains exactly one carboxyl group.

According to a further preferred embodiment, the carboxylic acid component contains less than 10 wt. %, preferably less than 5 wt. % of nitrogen-containing compounds, based on the total weight of the carboxylic acid component, nitrogen-containing compounds being both nitrogen-containing carboxylic acids and other nitrogen-containing organic compounds. The carboxylic acid component furthermore preferably does not contain nitrogen atoms (N).

According to a further preferred embodiment, the carboxylic acid component contains less than 10 wt. %, preferably less than 5 wt. % of aromatic ring compounds, based on the total weight of the carboxylic acid component, aromatic ring compounds being both carboxylic acids containing aromatic rings and other aromatic ring compounds. The carboxylic acid component furthermore preferably does not contain aromatic ring compounds.

According to a further preferred embodiment, the carboxylic acid component contains as non-metal atoms only non-metal atoms chosen from the group of carbon (C), oxygen (O), nitrogen (N) or hydrogen (H), preferably carbon (C), oxygen (O) or hydrogen (H), or several of these.

According to a further preferred embodiment, the carboxylic acid component contains less than 10 wt. %, preferably less than 5 wt. % of compounds containing hydroxyl groups, based on the total weight of the carboxylic acid component, compounds containing hydroxyl groups being both hydroxycarboxylic acids, and other organic compounds containing hydroxyl groups. The carboxylic acid component furthermore preferably does not contain hydroxyl groups.

According to a further preferred embodiment, the carboxylic acid component comprises a mixture of adipic acid, or an adipic acid derivative, as a dicarboxylic acid, and at least one monocarboxylic acid.

"Pure" and "technical grade oleic acid" can be employed as oleic acid. A pure oleic acid is understood as meaning a composition which contains more than 98 wt. % of oleic acid. A "technical grade oleic acid" is understood as meaning a composition which contains oleic acid to the extent of 98 wt. % or less. Such a technical grade oleic acid contains e.g. oleic acid in a range of from 60 to 75 wt. %, linoleic acid in a range of from 5 to 20 wt. % and stearic acid in a range of from 0 to 5 wt. %, based on the total weight of the technical grade oleic acid, the sum of the percentages by weight being 100. A suitable technical grade oleic acid is marketed e.g. by Cognis Oleochemicals GmbH, Germany, under the name "Edenor TiO5". Such a technical grade oleic acid which can preferably be employed can be obtained from animal fats, for example beef tallow. A technical grade oleic acid with a higher content of oleic acid can likewise be employed, e.g. with 80 to 95 wt. %, preferably 85 to 95 wt. % and furthermore preferably 90 to 95 wt. %, in each case based on the total composition. A technical grade oleic acid with 96 to 98 wt. % of oleic acid, based on the total composition, is very particularly preferred. Another technical grade oleic acid with approx. 80 to 90 wt. % of oleic acid, 2 to 10 wt. % of linoleic acid, 2 to 6 wt. % of stearic acid and 2 to 6 wt. % of palmitic acid, based on the total weight of the other technical grade oleic acid, is furthermore preferred, the sum of the percentages by weight being 100. Such another technical grade oleic acid is marketed e.g. as "high oleic" sunflower oil or HO sunflower oil.

According to a further preferred embodiment, pentaerythritol dioleate can be prepared from oleic acid as the carboxylic acid component and pentaerythritol as the alcohol component. In addition to pentaerythritol and pure oleic acid, technical grades thereof can also be employed as reactants in this process. If technical grades are employed, a product which contains at least 40, preferably at least 50, particularly preferably at least 60, and moreover preferably at least 70 wt. %, in each case based on this product, of pentaerythritol dioleate is usually obtained.

According to a further preferred embodiment, a partial ester is prepared as the ester, wherein either
  I. an alcohol component with two or more hydroxyl groups is reacted with a carboxylic acid component with one carboxyl group,
  II. a carboxylic acid component with two or more carboxyl groups is reacted with an alcohol component with one hydroxyl group, or
  III. a carboxylic acid component with two or more carboxyl groups is reacted with an alcohol component with two or more hydroxyl groups.

The term "partial ester" as used herein describes an ester of at least one carboxylic acid component and at least one alcohol component, where either
α.1) some of the hydroxyl groups of the alcohol component, for example in a range of from 20% to 80%, still more preferably from 25% to 75%, moreover preferably from 30% to 70%, still more preferably from 40% to 60%, and most preferably from 45% to 55% of the hydroxyl groups originally present in the alcohol component are still present as hydroxyl groups after the esterification reaction, or
α.2) some of the carboxyl groups of the carboxylic acid component, for example in a range of from 20% to 80%, still more preferably from 25% to 75%, moreover preferably from 30% to 70%, still more preferably from 40% to 60%, and most preferably from 45% to 55% of the carboxyl groups originally present in the carboxylic acid component are still present as carboxyl groups after the esterification reaction, and consequently are not esterified.

The term "full ester" accordingly describes an ester from the acids of the at least one carboxylic acid component and the at least one alcohol component, in which either
β.1) less than 20%, more preferably less than 10%, still more preferably less than 5%, moreover preferably less than 3%, still more preferably less than 2%, still more preferably less than 1% and most preferably less than 0.5% of the hydroxyl groups originally present in the alcohol component are still present as hydroxyl groups after the esterification reaction, or
β.2) less than 20%, more preferably less than 10%, still more preferably less than 5%, moreover preferably less than 3%, still more preferably less than 2%, still more preferably less than 1% and most preferably less than 0.5% of the carboxyl groups originally present in the carboxylic acid component are still present as carboxyl groups after the esterification reaction.

According to a further preferred embodiment, sebacic acid di(n-butyl) ester can be prepared from sebacic acid as the carboxylic acid component and n-butanol as the alcohol component.

According to a further preferred embodiment, stearic acid isobutyl ester can be prepared from stearic acid as the carboxylic acid component and 2-butanol as the alcohol component.

According to a further preferred embodiment, stearic acid butyl ester can be prepared from stearic acid as the carboxylic acid component and 1-butanol as the alcohol component.

According to a further preferred embodiment, a complex ester can be prepared from a mixture comprising adipic acid, palmitic acid and stearic acid as the carboxylic acid component and pentaerythritol as the alcohol component. Preferably, a mixture of 10 to 30 wt. % of adipic acid, 30 to 45 wt. % of palmitic acid and 40 to 50 wt. % of stearic acid, based on the carboxylic acid component, can be employed, the sum of the percentages by weight being 100. It emerges from this that a complex ester in the context of this invention is a mixture of two or more individual esters which, although generally present in the pure form, can occasionally contain small amounts of impurities which differ from esters.

According to a further preferred embodiment, trimethylol iso-nonanoate can be prepared from i-nonanoic acid as the carboxylic acid component and trimethylolpropane as the alcohol component. Instead of i-nonanoic acid, a $C_{8/10}$-carboxylic acid fraction which is obtainable in the preparation of fatty acids from plant or animal fats and in which the content of $C_8$- and $C_{10}$-carboxylic acid in each case independently is in a range of 40-50 wt. % can also be employed, According to a further preferred embodiment, a complex ester I from 30 to 70 wt. % of i-nonanoic acid, 10 to 40 wt. % of a $C_{8/10}$-carboxylic acid fraction and 2 to 30 wt. % of dimer acid (mixture of isomeric dimers from $C_{18}$-fatty acids, Pripol™ 1022, Uniqema, Gouda, Holland) as the carboxylic acid component and 10-30 wt. % of pentaerythritol dimer as the alcohol component can be employed, the sum of the percentages by weight being 100.

According to a further preferred embodiment, a sebacic acid dioctyl ester can be prepared from sebacic acid as the carboxylic acid component and 2-ethylhexanol as the alcohol component.

According to a further preferred embodiment, the ester has between 1 and 6 ester groups.

According to the invention, at least two different catalysts are employed, where at least in each case one of the at least two different catalysts is an electron donor and a sulphur-containing proton donor. Such catalyst combinations often have a high catalytic activity at temperatures which are lower compared with the high temperature catalysts, e.g. between 140 and 180° C., or between 120 and 185° C. At the same time, a smaller amount of by-products which appear coloured, in particular a smaller amount of substances which have a yellowish or brownish colouring, is formed. In principle, any catalyst mixture which is known from the above-mentioned catalyst groups to the person skilled in the art and appears to be suitable for catalysis of the esterifications according to the invention is suitable here.

Preferably, the catalyst, or a catalyst mixture, is employed in a range of from 0.0001 to 5 wt. %, preferably from 0.0005 to 4 wt. %, further preferably from 0.001 to 3.5 wt. %, moreover preferably from 0.004 to 3.0 wt. %, in each case based on the total amount of process components a. and b. Particularly preferably, the amount of catalyst added is in a range of from 0.006 to 2.5 wt. %, from 0.008 to 2.2 wt. %, from 0.01 to 2.5 wt. %, from 0.01 to 2.0 wt. %, from 0.03 to 1.8 wt. %, from 0.05 to 1.4 wt. % or from 0.05 to 1.2 wt. %, in each case based on the total amount of process components a. and b. A range of from 0.01 to 1.0 wt. %, from 0.01 to 0.7 wt. %, from 0.01 to 0.4 wt. % or from 0.01 to 0.2 wt. %, or to 0.1 wt. %, in each case based on the total amount of process components a. and b., is still more preferable.

According to a further preferred embodiment, the amount of electron donor, based on the total amount of catalysts, is more than 12.5 wt. %, preferably more than 20 wt. %, or most preferably more than 25 wt. %.

A suitable catalyst from the group of sulphur-containing proton donor is, for example,
  aa. sulphuric acid, or
  bb. an aliphatic, cycloaliphatic or aromatic $C_1$- to $C_{10}$-sulphonic acid, particularly preferably chosen from the group consisting of p-toluenesulphonic acid, o-toluene-sulphonic acid, methanesulphonic acid or trifluoromethanesulphonic acid,
  or a combination of two or more of these.

A suitable catalyst from the group of electron donor is, preferably,
  aa) metal,
  bb) a metal compound, or
  cc) a reducing acid,
  or a combination of two or more of these.

It therefore corresponds to an embodiment of the inventive process, that
  aa) a metal chosen from the group consisting of: titanium, tin, zirconium, in particular tin, or
  bb) a metal compound chosen from the group consisting of: tetraalkyl titanate, organotitanium complex, titanium salt, tin alkanoate, tin tetraalcoholate, organotin complex, zirconium salt, organozirconium complex, in particular tin alkanoate and organotin complex, such as tin octoate, tin oxalate or dibutyltin dilaurate, or
  cc) a reducing acid chosen from the group consisting of: sulphurous acid, hypophosphorous acid, phosphorous acid,
or two or more of these, is chosen as the electron donor.

Tin, titanium, zirconium, which are preferably employed as finely divided metal powders, are suitable as a metal. The salts, oxides or soluble organic compounds of the metals described above, or a mixture of at least two of these, are suitable as the metal compound. In contrast to the sulphur-containing proton donors, the metal compounds are high temperature catalysts which as a rule achieve their full activity only at temperatures above 180° C. According to the invention, a catalyst chosen from a) one or more divalent tin compounds, or b) one or more tin compounds and elemental tin, which can react with the reactants to give divalent tin compounds, is particularly preferred. For example, tin, tin(II) chloride, tin(II) sulphate, tin(II) alcoholates, or tin(II) salts of organic acids, in particular of mono- and dicarboxylic acids, e.g. dibutyltin dilaurate, dibutyltin diacetate, or a mixture of at least two of these, can be employed as the catalyst. Tin(II) oxalate and tin(II) octoate are particularly preferred as a tin catalyst.

In principle any reducing acid which is known to the person skilled in the art and appears to be suitable is suitable as a catalyst of the group of reducing acids. Hypophosphorous acid, sulphurous acid, phosphorous acid, selenious acid, oxalic acid, ascorbic acid, or two or more of these, is particularly preferred.

A mixture comprising p-toluenesulphonic acid and a tin compound is furthermore particularly preferred as a catalyst mixture. According to a further preferred embodiment, the catalyst or the catalyst mixture does not contain tin oxide.

According to a further preferred embodiment, a mixture which comprises at least three catalysts from one or more of the abovementioned groups is employed as the catalyst.

According to a further preferred embodiment, a mixture of 0.001 to 1 wt. % of an electron donor of the group of metal or metal compound, 0.001 to 1 wt. % of a sulphur-containing proton donor and 0.001 to 1 wt. % of a second electron donor from the group of reducing acid, in each case based on the total amount of process components a. and b., can be employed as the catalyst. Particularly preferably, tin oxalate is chosen as the metal compound, p-toluenesulphonic acid is chosen as the sulphur-containing proton donor and hypophosphorous acid is chosen as the reducing acid.

According to a further preferred embodiment of the process according to the invention, a catalyst mixture of 5 to 50 wt. %, preferably 15 to 40 wt. % of tin oxalate, 12.5 to 50 wt. %, preferably 15 to 40 wt. % of hypophosphorous acid, and 30 to 90 wt. %, preferably 40 to 65 wt. % of p-toluenesulphonic acid, which can be chosen in each case independently of each other, is employed, wherein the sum of all the wt. % is 100.

The process according to the invention for the preparation of an ester from a carboxylic acid component and an alcohol component can be carried out in the presence of further additives, for example one or more stabilizers, antioxidants, viscosity regulators and mixtures thereof.

In the context of carrying out the process according to the invention, process components a., b., d. and optionally c. are first employed in process step i. The sequence and the nature and manner of the addition of the individual components a., b., d. and optionally c. into the reactor in principle is not critical. Preferably, all the process components required for a reaction which are to be attributed to one of the groups chosen from alcohol component, carboxylic acid component and catalyst are in each case introduced into the reactor as process components within the particular group at least partly at the same time. In this context, the carboxylic acid components and alcohol components envisaged for the preparation of the ester according to the invention can be initially introduced and can then be reacted in the presence of a suitable catalyst or a suitable catalyst mixture. Furthermore, in a preferred embodiment the catalyst components are initially introduced together with one of the process components chosen from one of the groups of alcohol components or carboxylic acid components and the other components are then added. If the catalyst components are introduced into the reactor together with a process component, this can be effected by simultaneous introduction, and by introduction as a mixture, solution, suspension or dispersion.

Process components a., b., d. and the additives c. are provided in the reactor in liquid or in solid form. It may be preferable in the case of process components to be provided which are solid at the ambient temperature to be liquefied by heating. It is conceivable both that the liquefying is carried out in the course of providing the components, e.g. by means of a preheating stage, and that these process components are stored in liquid form at elevated temperature and are led from the holding place under thermostatic control and in an insulated line through a metering device. The addition of the process components in liquid form makes simple metering possible and promotes swift mixing of the process components introduced into the reactor.

Suitable metering devices are in principle all the devices which are known to the person skilled in the art and appear to be suitable. Electrically controllable shut-off valves or delivery pumps are particularly suitable.

The addition of the additives c. is in general carried out in a separate step to the components a., b. and d. already initially introduced. If these are solids, these are preferably introduced through a sluice at the upper side of the reactor, the contents of the reactor being stirred vigorously. A cellular wheel sluice can particularly preferably be employed as the sluice. It is often advantageous to mix the components, while stirring, in the context of providing them.

If at least one catalyst or a catalyst mixture is employed as an additive, a mixture of solids, a suspension or a liquid mixture is preferably employed. Preferably, the catalyst or the catalyst mixture is added only at the start of the reaction.

The reaction of the process components in process step ii. of the process according to the invention can be carried out by all processes which are known to the person skilled in the art and appear to be suitable. In this context, it may be advantageous to remove the water formed in the reaction from the reaction mixture, this removal of the water preferably being carried out by distillation, optionally by distillation with alcohol employed in excess, during the reaction.

Alcohol which has not reacted after the reaction has been carried out can also be removed from the reaction mixture, this removal of the alcohol preferably being carried out by means of distillation. When the reaction has ended, in particular after the unreacted alcohol has been separated off, the catalyst present in the reaction mixture can furthermore be separated off by washing with water, a filtration or by centrifugation, optionally after treatment with a base.

It is furthermore preferable to carry out the reaction of the process components at a temperature in a range of from 80 to 185° C., particularly preferably in a range of from 100 to 185° C. and very particularly preferably in a . . . [sic], and most preferably in a range of from 120 to 165° C.

According to a further preferred embodiment, the process according to the invention, in particular the reaction, is carried out at least in part under a reduced pressure in a range of from 1 to 800 mbar. Particularly preferably, the reduced pressure is in a range of from 2 to 700 mbar, or is 10 to 550 mbar, or 15 to 500 mbar. Most preferably, the pressure at least in a part of the process according to the invention, in particular during the reaction, is between 3 and 400 mbar.

It is furthermore preferable to carry out the reaction under reduced pressure at a temperature in a range of from 50 to 300° C., particularly preferably in a range of from 100 to 250° C. and very particularly preferably in a range of from 100 to 280° C., most preferably in a range of from 130 to 250° C. and furthermore preferably in a range of from 140 to 200° C. The preferred temperatures depend on the alcohol component chosen, the progress of the reaction, the catalyst mixture and the catalyst concentration. These can be easily determined by experiments for each individual case.

It is furthermore preferable to keep the process components uniformly mixed by stirring during the reaction.

According to a further preferred embodiment, a part of the process components is removed continuously from the reactor during the reaction, fed via a delivery line to an external flow-through heat exchanger and then fed back into the reactor. The external flow-through heat exchangers can be configured in any manner which is known to the person skilled in the art and appears to be suitable. Preferably, a plate heat exchanger, a tube bundle heat exchanger or a falling film evaporator or a combination of at least two of these, particularly preferably at least one falling film evaporator, can be employed as the flow-through heat exchanger. Furthermore, the outflow of the flow-through heat exchanger is connected to the reactor preferably via a return line of not more than 300 cm to 1 cm length, particularly preferably less than 200 cm to 10 cm length, most preferably less than 100 cm to 40 cm length. Particularly preferably, the outflow from the flow-through heat exchanger is connected directly, preferably via a flange, to the upper side of the reactor.

It is furthermore preferable in connection with the process according to the invention for the ester A obtained in the reaction ii. to be after-treated.

"After-treatment" is understood as meaning all conceivable steps and processes which are familiar to the person skilled in the art and which can be undertaken in order to purify the ester A obtained in process step ii. from by-products, impurities, catalysts and other additives or those processes with which the ester A is further processed to an end product.

These are understood as meaning, in particular, distillation, sorption, filtration, bleaching, centrifugation, washing, crystallization or drying processes, and continuing reactions, or a combination of at least two or more of these. Pressure filtration, bleaching and spray drying processes are preferred. According to a further preferred embodiment, no steam distillation is carried out as an after-treatment step.

In connection with the esters which can be prepared from a carboxylic acid component and an alcohol component with several hydroxyl groups in the process according to the invention, it is furthermore preferable for not all the hydroxyl groups of the alcohol component to be esterified, so that some of the hydroxyl groups remain non-esterified. In this connection, it is particularly preferable for from 5 to 80 mol %, particularly preferably from 10 to 70 mol %, still more preferably from at least 20 to 50 mol %, moreover preferably from 30 to 40 mol % and most preferably from 45 to 55 mol % of the hydroxyl groups of the alcohol component not to be esterified. This means that in the ester obtainable by reaction of the composition according to the invention, the content, described in mol %, of all the hydroxyl groups originally present in the alcohol component containing several hydroxyl groups for the preparation of the ester from a carboxylic acid component and an alcohol component is not esterified, and thus is also present as hydroxyl groups in ester A, and optionally also in the after-treated ester A.

The present invention also provides a device comprising as device units connected in fluid-conducting manner α) at least one reactant reservoir,
β) a reactor,
γ) a working up unit,
wherein there are at least two different catalysts in the reactor,
wherein
αα) at least one of the catalysts is chosen from the electron donor and
ββ) at least one of the catalysts is chosen from the sulphur-containing proton donor.

In principle, all reactor types known to the person skilled in the art which this person considers suitable for carrying out the process according to the invention can be employed. Preferably, a stirred tank on the side wall of which is arranged a heating jacket on the outside or inside is employed as the reactor. The heating jacket can be arranged on a part of the side wall or on the entire side wall. Preferably, the heating jacket is arranged on the entire side wall. Furthermore, the heating jacket particularly preferably can be controlled in sections. For example, the heating jacket is in 3, 4, 5 or more sections, each of which can be heated independently of each other. For transportation of heat, a heat transfer medium is led to the heating jacket through heating lines. All the usual heat transfer media known to the person skilled in the art are suitable as the heat transfer medium. The heat transfer medium can be either a heating means or a coolant. The heat transfer medium can also be under pressure. Preferably, heating steam, thermal oil or water, particularly preferably heating steam, is chosen as the heat transfer medium.

Furthermore, the reactor advantageously has a stirrer with a stirrer motor, transmission and stirrer shaft with stirrer blades, which is arranged on the upper side of the stirred tank, preferably centrally. The length of the stirrer shaft, the number of stirrer tiers arranged on the stirrer shaft, the diameter of these stirrer tiers and the geometry of the stirrer blades arranged in each stirrer tier are advantageously chosen such that during operation a uniform mixing of the process components, and where appropriate of the reaction products, is ensured, especially in the regions close to the base. The length of the stirrer shaft is preferably chosen such that the stirrer shaft extends from a motor lying outside the reactor, or from a transmission driven by a motor, almost to the base of the reactor. Preferably, the length of the stirrer shaft is chosen such that a distance of between about 5 to about 10%, with respect to the height of the reactor tank, remains between the end of the shaft and the reactor base. The stirrer shaft can be mounted on one side or, if the stirrer shaft is constructed to the reactor base, mounted at two points.

All stirrer types known to the person skilled in the art which this person considers suitable for carrying out the process according to the invention can be employed as stirrers. Preferably, stirrer types which have the effect at least in part of axial mixing during operation can be employed in particular. The stirrers can have one or more stirrer tiers, preferably one, 2, 3, 4, 5, 6 or 7 tiers. With respect to the geometry, cross, angled blade or disc stirrers with suitable stirrer blades are particularly preferred, and MIG or INTERMIG stirrers are most preferred. In the case of angled blade, disc and MIG stirrers, the stirrer blades in adjacent tiers can be displaced by 90° in the horizontal plane. The stirrers particularly preferably have an even number of tiers.

The stirrers are preferably produced from steel, preferably from V2A or V4A steel, particularly preferably from the following materials, the material numbers being found in EN10088: 1.4307, 1.4306, 1.4311, 1.4301, 1.4948, 1.4404, 1.4401, 1.4406, 1.4432, 1.4435, 1.4436, 1.4571, or 1.4429, particularly preferably 1.4301 or 1.4571.

The stirrer can moreover be at least partly coated with a surface coating composition. Preferably, the stirrer is equipped with a polymer coating. For example, a fluoropolymer coating which protects the material from which the stirrer is made from the fluid or mixture to be stirred is suitable as a polymer coating.

Preferably, a ratio of the diameter of the stirrer tier(s) to the diameter of the reactor of from 0.55 to 0.75, particularly preferably 0.60 to 0.70 or 0.62 to 0.68, very particularly preferably 0.64 to 0.66, e.g. 0.65, is chosen. By suitable choice of the parameters, the person skilled in the art ensures complete mixing and mingling in the reactor and avoids a deposit of solid constituents.

The stirrer blades can have the most diverse geometries, the geometry influencing the nature of the mixing. The "nature of the mixing" is understood as meaning the polar vector acting on the stirred mixture due to the movement of the stirrer. The polar vector has vertical and horizontal contents. Usually, both contents are not equal to zero. For example, a cross stirrer with stirrer blades arranged axially to the stirrer shaft and aligned vertical to the stirrer plane has the effect of rather horizontal mixing, whereas a cross stirrer with stirrer blades arranged at an angle, e.g. axially, to the stirrer shaft and at an angle of 30°, 45° or 60° with respect to the stirrer plane has the effect of a more vertical mixing. It is furthermore conceivable to provide a spiral stirrer.

Stirrers of which the stirrer blades have, with respect to the stirrer plane, a positive incline in the region close to the stirrer shafts, preferably the inner two thirds of the stirrer blade, and a negative incline in the region away from the stirrer shafts, preferably the outer third of the stirrer blade, are particularly preferred.

The incline of a stirrer blade is understood as meaning its alignment with respect to the stirrer plane, a positive incline meaning that the stirrer blade rises in the direction of rotation from its front edge from the bottom upwards to its rear edge, and has the effect of an ascending flow of material. A negative incline means that the stirrer blade drops in the direction of rotation from its front edge from the top downwards to its rear edge, i.e. has the effect of a descending flow of material. Such a stirrer has the effect of vertical mixing from the bottom upwards in the region of the middle of the reactor and a vertical mixture from the top downwards at the reactor wall.

The type of mixing described above can be assisted and adapted with further auxiliary devices. For example, baffles can be provided on the inside wall of the reactor. These are preferably attached to the inside wall of the reactor in the vertical direction, the plane in which the baffle lies being aligned through or at least in the direction of the vertical axis of the reactor.

According to another example, end stirrer organs which are moved a short distance above the reactor base can be attached on the lower stirrer tier. A short distance is to be understood as meaning so small that deposits of solid on the bottom can be carried along and/or swirled up by the stirrer. In this context, the end stirrer organs have the effect of a horizontal mixing to the extent of at least 50%, preferably 70%, based on the layer mixed by the end stirrer organs. The end stirrer organs preferably have a flat shape, the sides of the flat shape which are adjacent to the reactor base and the reactor wall being designed such that an essentially constant gap is provided between the reactor base and the reactor wall. If the reactor base is curved, for example, the end stirrer organs have a surface which is at least rounded at the side, and optionally an angled position of the end stirrer organs. Preferably, the end stirrer organs sweep over the reactor base at a distance of from 10 to 30 cm, preferably 15 to 25 cm or 30 cm.

In principle all materials which are known to the person skilled in the art and which this person considers suitable with respect to carrying out the process according to the invention, in particular with respect to strength, elasticity and corrosion resistance, can be employed as the material for production of the devices described above. In particular, the materials which are preferred in the choice of material for the stirrer are also preferred. Rustproof steel, preferably from V2A or V4A steel, in particular from the following materials, are preferably employed for production of the reactor, the material numbers being found in EN10088: 1.4307, 1.4306, 1.4311, 1.4301, 1.4948, 1.4404, 1.4401, 1.4406, 1.4432, 1.4435, 1.4436, 1.4571, or 1.4429, particularly preferably 1.4301 or 1.4571.

The device furthermore has a working up unit. Any device which is known to the person skilled in the art and appears to be suitable for improving a certain parameter of the crude product obtained in the reaction can be conceived as the working up unit. For example, a purification or separating device can be provided as the working up unit. Devices which have both a purifying and a separating action are usual in particular. Distillation units, filters, filter presses, sieves, separators, clarification devices or centrifuges, or a combination of two or more of these, are preferably suitable as working up units.

A line for removing a gaseous fluid stream which, for example, can remove by-products with a molecular weight of less than 100 g/mol is furthermore preferably provided on the reactor, this line being connected, if desired, to a pressure reducing unit for applying a reduced pressure. The fluid stream can furthermore be further treated, and for this led over at least one heat exchanger in order to cool the fluid stream. In this context, at least a part of the fluid stream can pass into a liquid phase, which is often collected and led back into the reactor or removed. In this context, at least a part of the fluid stream can pass into a liquid phase, which is often collected and led back into the reactor or removed. This treatment of the fluid stream can be repeated twice or more often. If the fluid stream is led over at least two heat exchangers arranged in series, in the first heat exchanger a part of the fluid stream which differs from that in the at least second heat exchanger can pass into a liquid phase. It is thus possible, if desired, to lead a part of the fluid stream back into the reactor as a liquid phase and to discard another part of the fluid stream. Furthermore, the part of the fluid stream which is to be led back into the reactor as a liquid phase can optionally be divided into two immiscible phases in a separator with the aid of an adjustable removal device. Such a removal device is configured, for example, as an interfacial layer regulator. The first phase can then be passed back into the reactor via a return line. Alternatively, the entire fluid stream can be drained off and e.g. fed to another use, or discarded. The division of the fluid in the separator into two immiscible phases is carried out by appropriate alignment of the interfacial layer regulator. In principle any known embodiment which appears to be suitable to the person skilled in the art is suitable as the interfacial layer regulator.

It is furthermore conceivable to collect the fluid stream in a receiver before introduction into the separator, to lead the fluid stream over an additional heat exchanger and to further cool it in this way. At a lower temperature of the fluid stream, a better and faster demixing of at least two immiscible, liquid phases can be observed.

A heat transfer medium is led through each of the heat exchangers already mentioned. In order to effect cooling of the fluid stream, cooling fluids are preferably employed as heat transfer media. Preferably, the highest possible temperature difference is chosen between the fluid stream to be liquefied and the cooling fluid, in order to achieve marked cooling of the fluid stream. Furthermore, it may be entirely desirable to cool the fluid stream in a first step merely to a first temperature at which a part of the fluid stream is liquefied, before a further part of the fluid stream is liquefied in a downstream heat exchanger. It is conceivable that a first heat exchanger is operated with a cooling fluid which, for example, is at 20 or 25° C., or has a higher temperature, in order to separate off from the fluid stream at least a high-boiling content of the fluid stream which, e.g. has a boiling point in a range of from 80 to 120° C.

In this connection, a high-boiling content is understood as meaning one or more components of the fluid stream which have a boiling point in a range of from 50 to 150° C., preferably from 60 to 140° C., very particularly preferably from 70 to 130° C. In particular, a high-boiling content is understood as meaning those components which have a boiling point of from 80 to 160° C., in particular from 90 to 200° C. or more.

According to a further, preferred embodiment, the reactor can have on its under-side an outlet which is connected to a delivery pump by fluid-conducting means. In principle, all pumps known to the person skilled in the art which this person considers suitable for carrying out the process according to the invention, taking into account the properties of the liquid to be delivered, which is optionally also in the form of a suspension, dispersion or emulsion, are suitable as the delivery pump. Preferably, a centrifugal, reciprocating, screw, impeller or hose pump can be employed. A centrifugal pump is very particularly preferred.

According to a further preferred embodiment, a delivery line from the delivery pump is connected to an external heat exchanger by fluid-conducting means, the external heat exchanger being connected to the reactor, preferably to the upper side thereof, by fluid-conducting means. The external heat exchanger is connected to the reactor preferably via a return line of not more than 300 cm to 1 cm length, particularly preferably less than 200 cm to 10 cm length, most preferably less than 100 cm to 40 cm length. Particularly preferably, the external heat exchanger is connected directly, preferably via a flange, to the upper side of the reactor. A plate or tube bundle heat exchanger or a falling film evaporator, or a combination of two or more of these, can be employed as the heat exchanger. A falling film evaporator is preferred.

By the use of an external heat exchanger, the introduction of energy into a delivery stream led via this can be established better both with respect to the duration of the introduction and with respect to the amount of energy, i.e. the heat supplied or removed. This form of introduction of energy renders possible a short duration of the introduction, and therefore little or no change at all to the substance treated in the heat exchanger, in the case of heat-sensitive substances, that is to say those which readily decompose or change. Furthermore, with the use of an external heat exchanger an advantageous ratio of heat transfer area in the heat transfer zone of the heat exchanger to reactor volume can be established.

The delivery stream is preferably led over the heat transfer surface as a film. In this case, the delivery stream has a low height above the heat transfer surface. This arrangement renders possible both a high and a uniform energy transfer rate, so that short energy introduction times are possible compared with other heat transfer arrangements or heat transfer devices. The exposure of the process components to heat in the delivery stream is therefore reduced. Furthermore, undesirable side reactions, e.g. oxidation or polymerization, can likewise be reduced or even avoided.

By suitable choice of the dimensions of the heat transfer surface, in particular of the zone in the flow direction swept over by the film, the volume throughput of the delivery stream and the amount of energy introduced into this can be adapted to the circulation throughput, and thus to the requirements of the process according to the invention. Preferably, a high ratio of heat transfer area in the heat exchanger to volume throughput of the delivery stream is chosen. Furthermore, a ratio of heat transfer area to volume throughput of the delivery stream in a range of from 15 to 1 h/m, particularly preferably from 5 to 1.1 h/m, further preferably from 2 to 1.3 h/m and most preferably from 1.7 to 1.4 h/m is preferred.

For example, the external heat exchanger can be configured as a falling film evaporator. In this case, on entry into the heat exchanger the delivery stream is divided and applied as a film to the inner surfaces of tubes connected to the falling film evaporator inlet by fluid-conducting means and preferably arranged side by side, the tube walls forming the heat transfer surfaces. The sum of the individual heat transfer surfaces of the individual tubes forms the heat transfer surface of the falling film evaporator. On passage of the divided delivery stream from the tube into the outflow of the falling film evaporator, the delivery stream is combined again.

The amount of energy per unit volume of the delivery stream which can be transferred in the heat exchanger is determined by the speed of the delivery stream, the distance flowed over in the direction of flow on the heat transfer surface and by the average thickness of the film when sweeping over the heat transfer surface. The thickness of the film means the height of the film over the heat exchanger surface. Preferably, the thickness of the film is in a range of from 2 to 20%, particularly preferably from 5 to 15%, and furthermore from 7 to 12%, in each case based on the internal diameter of the heat transfer surface constructed as tubes.

A further outlet can be positioned on the reactor underside. The ester A can be removed from the reactor via this, e.g. by a second delivery pump, after the reaction has ended or been discontinued, and fed to a further processing stage, e.g. a filling unit, a heat exchanger, a processing and/or working up unit. Preferably, in the context of that said so far, the under-side of the reactor has an outlet via which both the delivery stream during the reaction and the ester A are led out of the reactor. In order both to be able to lead the process components over an external heat exchanger as a delivery stream during the reaction, and to be able to lead the ester A via the same outlet after the reaction in the reactor, a delivery pump on the outlet of which a distributing device is arranged is preferably provided on the outlet of the reactor. Several connections leading away are provided on this distributing device, at least a first connection being connected by fluid-conducting means to the external heat exchanger and a second connection to a feed to a further processing stage.

According to a further preferred embodiment, a working up unit is provided as a further processing stage. This often comprises a working up container and optionally further devices. All embodiments which are known to the person skilled in the art and appear to be suitable are possible as the working up container. Preferably, the working up container has a tank with a stirrer and heating jacket, it being possible for the heating jacket to be arranged on the inside or outside. In such a working up container, an after-treatment of the crude product or the product can be carried out without prolonging the occupancy of the reactor.

The reactor can furthermore have at least one reactant reservoir. Any desired installations in which process components can be kept ready before the reaction are conceivable as the reactant reservoir. A storage container, a tank, a boiler or a still is preferred. It is likewise possible to provide a storage container connected to a further production plant as the reactant reservoir.

According to a further, preferred embodiment, the reactant reservoir is connected to the reactor via a line which is led via a preheating stage. All devices known to the person skilled in the art which this person considers suitable for achieving this aim in carrying out the process according to the invention can be employed as the preheating stage. A plate or tube bundle heat exchanger, or a combination of two or more of these, is particularly suitable as the preheating stage. A tube bundle heat exchanger is preferred.

According to a further, preferred embodiment, the reactant reservoir is temperature-controllable, for example by a heating jacket or cooling jacket for the reactant reservoir. It may be desirable here for a substance which is solid at the ambient temperature to be kept ready above its melting point. If this substance is present in liquid form, simple, often also more accurate metering than e.g. in the case of metering of the solid is possible. Furthermore, by leading substances in closed lines, the risk of exposure and contamination of employees and the environment is avoided.

Preferably, the reactor is furthermore connected to a pressure reducing unit. This is preferably arranged in a fluid-carrying continuation of the heat exchanger or heat exchangers and is connected to the end of the line for removal and/or treatment of the fluid stream. In principle all units for generating a reduced pressure which are known to the person skilled in the art are suitable as the pressure reducing unit, as long as he would consider them taking into account the reactor design.

In a preferred embodiment of the inventive device there is at least one carboxylic acid component with more than 6 carbon atoms in the reactor.

Preferably, the content of electron donor in the reactor, based on the total amount of catalysts in the reactor, is more than 12.5 wt. %.

It is preferred according to the invention that there are no polymerization inhibitors in the reactor.

In a preferred embodiment of the device according to the invention, catalyst in a range of from 0.01 wt. % to 0.5 wt. %, based on the total substances occupying the reactor, is provided in the reactor.

It is preferred according to the invention that
aa. sulphuric acid, or
bb. an aliphatic, cycloaliphatic or aromatic $C_1$- to $C_{10}$-sulphonic acid, or two or more of these, is provided as the sulphur-containing proton donor in the reactor.

Preferably a metal, a metal compound, or a reducing acid, or a combination of two or more of these, is provided as the catalyst of group I) in the reactor.

It is preferred in the device according to the invention that
aa) a metal chosen from the group of titanium, tin, zirconium, in particular tin, or
bb) a metal compound chosen from the group of tetraalkyl titanates, organotitanium complexes, titanium salts, tin alkanoates, tin tetraalcoholates, organotin complexes, zirconium salts, organozirconium complexes, in particular tin alkanoates and organotin complexes, such as tin octoate, tin oxalate or dibutyltin dilaurate, or
cc) a reducing acid chosen from the group consisting of sulphurous acid, hypophosphorous acid, phosphorous acid,
or a combination of two or more of these, is provided as the electron donor in the reactor.

Preferably the catalyst in the reactor is a mixture of
5 to 50 wt. % of tin oxalate,
12.5 to 50 wt % of hypophosphorous acid, and
30 to 90 wt. % of p-toluenesulphonic acid,
which can in each case be chosen independently of each other, wherein the sum of all the wt. % is 100.

An embodiment, which also contains optional features and is in no way intended to represent a limitation of that said so far is explained further by way of example in the following with the aid of drawings.

Figure 1:
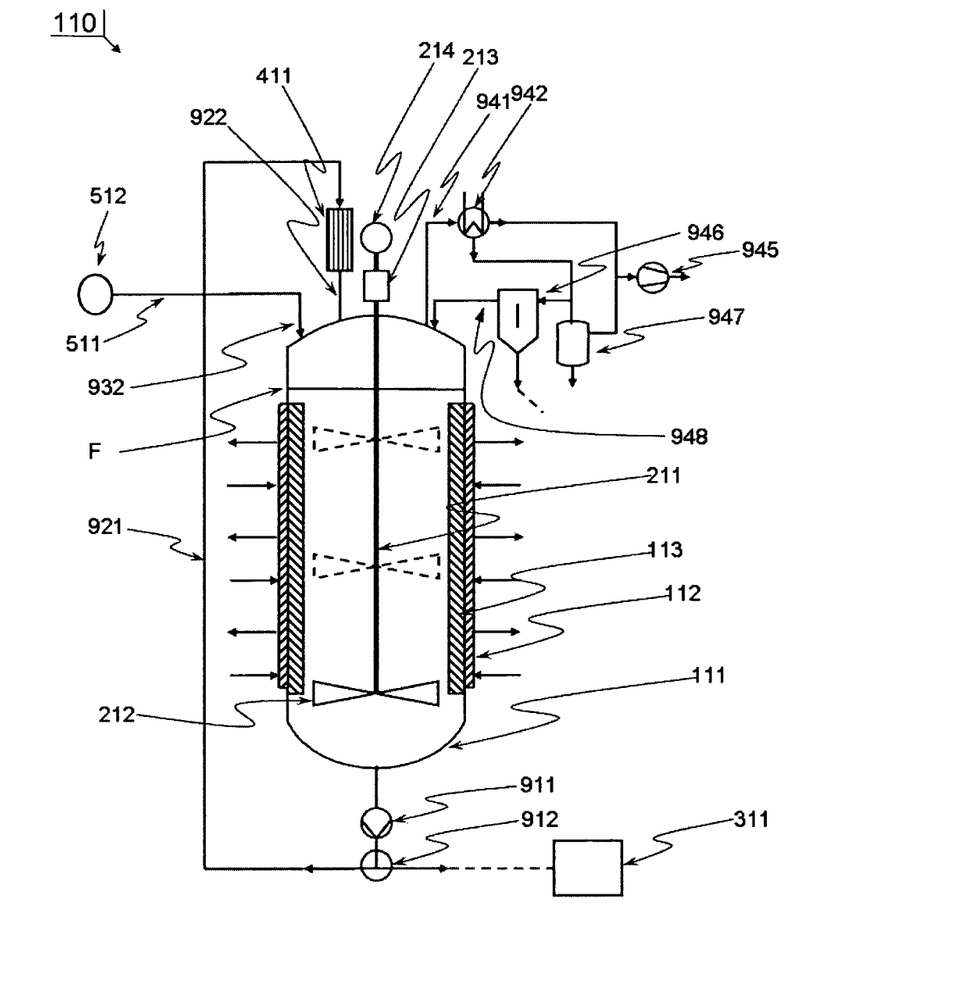

FIG. 1 shows a reaction region 110 with a reactor 111 with various installations which is suitable and preferred for carrying out the process according to the invention. The reactor 111 has on the reactor wall an external heating jacket 112. This is divided into three sections, which can be controlled separately. In the middle of the reactor, along its vertical axis, a stirrer 211 with stirrer tiers 212 is arranged. The stirrer 211 is driven via a transmission 213 with a motor 214. Baffles 113 can be arranged on the reactor wall. On the upper side of the reactor 111, an external heat exchanger 411 is arranged via a connection 922, which can be configured as a return line or as a flange. Preferably, the external heat exchanger 411 is configured as a falling film evaporator. On the under-side of the reactor 111 is an outlet with a shut-off valve, which is connected to a delivery pump 911. A distributing device 912, e.g. a multi-way valve, is attached to the outlet of the delivery pump. From the distributing device 921, a return line 921 leads to the external heat exchanger 411. A second line leads from the distributing device 912 to a working up unit 311. The filling level line F represents the position of the interface between the space underneath the interface taken up by the filling volume and the gas space above this.

On the upper side of the reactor 111, a feed line 511 is attached, which is connected to one or more further reactant reservoirs 512 containing process components. Furthermore, a line 941 for removing a fluid stream leads from the upper side of the reactor 111 to the heat exchanger 942. This line is connected to a second heat exchanger 943. One or more cooling fluids flow through the heat exchangers 942 and 943 at the same or a different temperature. The exits of the heat exchangers 942 and 943 are connected to a receiver 947 and a separator 946.

A condensate of the heat exchangers 942 and 943 can be fed either directly or via the receiver 947 and a further heat exchanger 944 to the separator 946. The separator 946 has an interfacial layer regulator, from which a return line 948 leads to the reactor 111. The separator 946 and the receiver 947 can likewise be emptied by an outlet in each case arranged on the under-side. A reduced pressure can be generated by a pressure reducing unit 945 via a line connected to the heat exchanger 944 and the receiver 947.

The present invention also provides a process for the preparation of a thermoplastic composition comprising
a1) a thermoplastic polymer,
b1) an additive, and
c1) optionally further additives,
comprising the process steps:
i) provision of a thermoplastic polymer or of a precursor of a thermoplastic polymer or both;
ii) provision of an additive comprising an ester obtainable by the process according to the invention described above by reaction of at least one alcohol component and at least one carboxylic acid component, the device according to the invention described above preferably being employed;
iii) optionally provision of further additives,
iv) mixing of components i), ii) and optionally iii).

Those esters and further additives which have already been mentioned above as preferred esters and further additives in connection with the processes according to the invention for the preparation of an ester are preferred as esters and further additives.

In a preferred embodiment, the additive comprises a preferably at least partly hardened ester from a carboxylic acid component and an alcohol component with one or more hydroxyl groups.

"Hardened esters" in the present case are understood as meaning esters in which the carboxylic acid components are derived from a carboxylic acid containing one or more double bonds. These double bonds can be at least partly or completely removed by hydrogenation. If not all of the double bonds of the carboxylic acid have been removed, a partly hardened ester is referred to, preferably at least 50 mol % and particularly preferably at least 70 mol % of the double bonds of the carboxylic acid having been hydrogenated, which can be determined, for example, by NMR spectroscopy or by determining the iodine number.

The term "thermoplastic polymer" is understood as meaning plastics which can be (thermo)formed (plastically) in a temperature range which is elevated with respect to room temperature. This operation is reversible and can be repeated by cooling and reheating into the molten state as often as desired, unless thermal decomposition of the material starts due to overheating.

Possible thermoplastic polymers which the composition according to the invention can contain are, in particular, thermoplastic polyurethanes, thermoplastic polyesters, thermoplastic polyamides, thermoplastic polyolefins, thermoplastic polyvinyl esters, thermoplastic polyethers, thermoplastic polystyrenes, thermoplastic polyimides, thermoplastic sulphur polymers, thermoplastic polyacetals, thermoplastic fluorinated plastics, thermoplastic styrene/olefin copolymers, thermoplastic polyacrylates, thermoplastic ethylene/vinyl acetate copolymers or mixtures of two or more of the above-mentioned thermoplastic polymers.

It is preferable according to the invention for the thermoplastic polymer to be based on thermoplastic polyesters to the extent of more than 90 wt. %, particularly preferably to the extent of more than 95 wt. %, moreover still more preferably to the extent of at least 99 wt. % and most preferably to the extent of 100 wt. %, in each case based on the total weight of the thermoplastic polymer. The term "polyester" as used herein includes in particular polymers which have been obtained by a polycondensation reaction between a polycarboxylic acid and a polyol (so-called "AA//BB polyesters") or by a polycondensation reaction of a hydroxycarboxylic acid or by ring-opening polymerization of a cyclic ether (so-called "AB polyesters"). In one embodiment according to the invention, polycarbonates which are obtainable by reaction of phosgene with diols may be excluded from the term "polyester" used according to the invention.

In principle, all the thermoplastic polyesters and copolyesters currently known can be used as component a1) in the thermoplastic composition according to the invention. Examples of such polyesters include linear polyesters which have been prepared via a condensation reaction of at least one polycarboxylic acid, preferably a dicarboxylic acid (dibasic acid) or an ester-forming derivative thereof, and at least one polyol, preferably a dihydric alcohol (diol).

It is furthermore conceivable to prepare polyesters which have a degree of branching or crosslinking which is not equal to zero, that is to say are not linear.

In this connection, the degree of branching is the mean, over the sum of all the polyester molecules, of the ratio of the number of branching monomer units to the total number of all the monomer units per polyester molecule. The degree of branching is in a range of from 0.01 to 50 wt. %, preferably from 0.05 to 30 wt. %, further preferably from 0.1 to 20 wt. %, particularly preferably from 0.5 or 1 to 10 wt. % and most preferably between 3 and 7 wt. %, based on the sum of all the thermoplastic polyester molecules. If polyesters which are not exclusively linear but are branched to at least a small proportion, e.g. between 2 and 8 wt. %, are employed as the thermoplastic polyester, an adaptation of the physical properties of the thermoplastic composition, for example a reduction of the viscosity, can be established.

In this connection, the degree of crosslinking is the mean, over the sum of all the polyester molecules, of the ratio of the number of crosslinking monomer units to the total number of all the monomer units per polyester molecule. In this connection, the degree of crosslinking is in a range of from 0.001 to 3 wt. %, preferably 0.005 to 1 wt. %, particularly preferably 0.01 to 0.5 wt. % and most preferably 0.05 to 0.1 wt. %, based on the sum of all the thermoplastic polyester molecules. At these low degrees of crosslinking, the thermoplastic properties of the molecules are retained.

The preferably difunctional acid and the preferably difunctional diol can both be either aliphatic or aromatic, aromatic and partly aromatic polyesters being particularly preferred as thermoplastic moulding materials because of their high softening points and stability to hydrolysis. In the case of aromatic polyesters, between 80 and 100% of all the ester linkages are added on to the aromatic rings.

These thermoplastic moulding materials can be semicrystalline and even show liquid crystal properties or be amorphous. According to the invention, partly aromatic polyesters which have been obtained from at least one aromatic dicarboxylic acid or an ester-forming derivative thereof and at least one aliphatic diol are particularly preferred thermoplastic polyesters. Examples of suitable aromatic dicarboxylic acids include terephthalic acid, 1,4-naphthalenedicarboxylic acid or 4,4'-biphenyldicarboxylic acid. Examples of suitable aliphatic diols include alkylene diols, specifically those which contain 2 to 6 C atoms, preferably 2 to 4 C atoms, where ethylene glycol, propylene diols and butylene diols are to be mentioned in particular here. Ethylene glycol, 1,3-propylenediol or 1,4-butylenediol are preferably used as the polyol or diol component for the preparation of the thermoplastic polyesters contained as component a) in the composition according to the invention. Thermoplastic polyesters which are obtainable by reaction of a dicarboxylic acid with a diol and are particularly preferred according to the invention include, in particular, polyalkylene terephthalates, for example polyethylene terephthalate (PET), polypropylene terephthalate (PPT) or polybutylene terephthalate (PBT), polyalkylene naphthalates, for example polyethylene naphthalate (PEN) or polybutylene naphthalate (PBN), polyalkylene dibenzoates, for example polyethylene dibenzoate, and mixtures of at least two of these thermoplastic polyesters.

The partly aromatic polyesters described above can optionally contain a small amount of units which originate from other dicarboxylic acids, for example isophthalic acid, or other diols, such as cyclohexanedimethanol, which in general reduces the melting point of the polyester. A specific group of partly aromatic polyesters are so-called segmented or block copolyesters, which in addition to the abovementioned polyester segments (also called "hard segments"), contain so-called "soft segments". These soft segments originate from a flexible polymer; that is to say one with amorphous contents with a low glass transition temperature ($T_g$) and low rigidity to the extent of 60 to 100 wt. %, preferably more than 70 and still more preferably more than 80 wt. % to 100 wt. %, based on the total weight of the polymer. This flexible polymer has reactive end groups, preferably two hydroxyl groups. Preferably, the glass transition temperature of these "soft segments" is below 0° C., particularly preferably below −20° C. and most preferably below −40° C. In principle, several different polymers can be used as the soft segment. Suitable examples of "soft segments" are aliphatic polyethers, aliphatic polyesters or aliphatic polycarbonates. The molecular weight of the soft segments can vary within wide limits, but is preferably between 400 and 6,000 g/mol.

In addition to the abovementioned linear polyesters which are obtainable via a polycondensation reaction of at least one polycarboxylic acid or an ester-forming derivative thereof and at least one polyol, the thermoplastic composition according to the invention can also contain thermoplastic polyesters which are obtainable by a polycondensation reaction of short-chain hydroxycarboxylic acids or by a ring-opening reaction of cyclic esters.

Examples of suitable short-chain hydroxycarboxylic acids which can be employed for the preparation of thermoplastic polymers include in particular L-lactic acid, D-lactic acid, DL-lactic acid, glycolic acid, 3-hydroxybutyric acid, 4-hydroxybutyric acid, 4-hydroxyvaleric acid, 5-hydroxyvaleric acid, 6-hydroxycaproic acid and mixtures of these hydroxycarboxylic acids. Examples of suitable cyclic esters include in particular glycolide (a dimer of glycolic acid) and ε-caprolactone (a cyclic ester of 6-hydroxycaproic acid).

The preparation of the thermoplastic polyesters described above is also described, inter alia, in "*Encyclopedia of Polymer Science and Engineering*", volume 12, pages 1 to 75 and pages 217 to 256; John Wiley & Sons (1988) and also in "*Ullmann's Encyclopedia of Industrial Chemistry*", volume A21, pages 227 to 251, VCH Publishers Inc. (1992). Thermoplastic polymers which are preferred according to the invention are polyethylene terephthalate (PET), polybutylene terephthalate (PBT) and polylactic acid (PLA), it being possible for a preferred embodiment of a thermoplastic composition of the present invention to contain each of this polymers in itself to the extent of more than 50 wt. %, preferably more than 75 wt. % and particularly preferably more than 90 wt. %, in each case based on the thermoplastic composition.

Components a1), b 1) and optionally c1) are first provided in process steps i), ii) and optionally iii). The mixing of components i), ii) and optionally iii) is then carried out in process step iv) of the process according to the invention.

In this context, the mixing of components a1), b 1) and optionally c1) can be carried out utilizing known techniques. Thus, the mixing can be, for example, a dry mixing operation, in which the various components are mixed at below the melt processing temperature of the thermoplastic polymer, or a melt mixing process, in which the components are optionally premixed, and mixed at the melt processing temperatures of the thermoplastic polymer. The melt mixing processes include, preferably, the melt kneading process, which can be realized, for example, by continuous melt kneading using a single-screw kneading machine, a twin-screw kneading machine of the toothed-same direction of rotation type, toothed-opposite direction of rotation type, nontoothed-same direction of rotation type, nontoothed-opposite direction of rotation type, or other types, or by batch melt kneading using a roller kneading machine, a Banbury kneading machine or similar. A combination of a dry mixing process and a melt mixing process is furthermore conceivable.

The sequence and the nature and manner of the addition of the individual components a1), b1) and optionally c1) into the mixing device is furthermore in principle not critical. Thus, for example, the thermoplastic polymer and optionally the additional substances can first be initially introduced into the mixing device and the additive only then added. It is also conceivable for the additive or a part of the additive first to be mixed with one or more other components of the thermoplastic composition according to the invention, for example with one or more additional substances, and then either for this mixture to be added to the thermoplastic polymer already in the mixing device, or for this mixture first to be initially introduced into the mixing device and the thermoplastic polymer only then to be added.

In further embodiments of the process according to the invention for the preparation of a thermoplastic composition, mixing is carried out in accordance with at least one of the following measures:

M1) at the glass transition temperature of the thermoplastic polymer or at a temperature above the glass transition temperature of the thermoplastic polymer;
M2) where the additive is more liquid than the thermoplastic polymer; or
M3) where at least a part of the additive is added to the precursor of the thermoplastic polymer.

Embodiments according to the invention furthermore include combining of two or more of the above measures. The following combinations of measures represented with the aid of the combinations of figures thus result specifically as embodiments: M1M2, M1M3, M2M3 and M1M2M3.

According to a preferred embodiment M1 of the process according to the invention, the mixing of components i), ii) and optionally iii) is carried out in process step iv) of the process according to the invention by a melt mixing process. In this connection it is preferable in particular for the mixing in process step iv) to be carried out at the glass transition temperature of the thermoplastic polymer or at a temperature above the glass transition temperature of the thermoplastic polymer. In this connection, it is particularly preferable for the mixing to be carried out at a temperature in a range of from 5° C. below the glass transition temperature ($T_g$) to 200° C. above the glass transition temperature of the thermoplastic polymer employed, particularly preferably at a temperature in a range of from 1° C. below the glass transition temperature ($T_g$) to 180° C. above the glass transition temperature of the thermoplastic polymer employed and most preferably at a temperature in a range of from 1° C. above the glass transition temperature ($T_g$) to 150° C. above the glass transition temperature of the thermoplastic polymer employed, the upper limit of the temperature range being essentially limited, however, by the decomposition temperature of the thermoplastic polymer employed. Embodiments according to the invention furthermore include mixing at temperatures in a range of from 10 to 180° C. and preferably 50 to 150° C. above the glass transition temperature of the thermoplastic polymer employed.

In embodiment M2 according to the invention, in which the additive is more liquid than the thermoplastic polymer, it is preferable for the additive to be employed at a temperature at which this is liquid and the thermoplastic polymer is not yet liquid. The temperature of the thermoplastic polymer here is preferably below the glass transition temperature of this polymer. It is thus preferable for the melting temperature of the additive and the glass transition temperature of the thermoplastic polymer to differ by at least 5° C., preferably at least 10° C. and particularly preferably at least 30° C. In this embodiment and also generally, it is furthermore preferable for the thermoplastic polymer to be employed as granules. In general, all granule forms known to the person skilled in the art with a spherical or cylindrical spatial shape are also possible in the present case. The granule size, determined by means of sieve analysis, is in a range of from 0.01 to 5 cm, and preferably in a range of from 0.1 to 4 cm for at least 70 wt. % of the granule particles. By the procedure according to this embodiment, the surfaces of the granule particles can be at least partly coated with the additive according to the invention, so that at least partly coated thermoplastic polymer granules are obtained. This allows a distribution of the additive according to the invention in the thermoplastic composition which is as homogeneous as possible, especially if this is made up as a formulation for the extrusion taking place later.

In embodiment M3 according to the invention, in which the additive is added to the precursor of the thermoplastic polymer, additive in the liquid form and also in the solid form are possible. Possible precursors of the thermoplastic polymer are in principle all the precursors before the thermoplastic polymer is obtained which are known to the person skilled in the art. These include, in particular, precursors which have a lower molecular weight than the final thermoplastic polymer. It is preferable here for the molecular weight of the precursor to differ from that of the finished thermoplastic polymer by a factor of at least 1.1, preferably at least 1.5 and particularly preferably at least by a factor of 2. In addition to the monomers and oligomers, which preferably comprise 2 to 100 monomers, employed for the preparation of the thermoplastic polymer, a prepolymer which is polymerized completely, usually by heat treatment, to give the finished thermoplastic polymer is included, especially in the case of polycondensates. The prepolymer is preferably based on more than 100 monomers as recurring units, the number of the monomers as recurring units and therefore the final molecular weight of the finished thermoplastic polymer not being reached. It is therefore particularly preferable for the additive according to the invention in each case to be added to the monomers, oligomers or the prepolymer or at least two of these. By this means, in addition to a homogeneous distribution of the additive according to the invention, incorporation of the additive by chemical bonds with the thermoplastic polymer is also achieved, usually by the conditions prevailing during the polymerization or complete polymerization.

If the heated composition obtained in process step iv) in the case of a melt mixing process is not fed directly to the production of shaped articles, the process can also additionally include the further process step v):

v) cooling of the thermoplastic composition, preferably to a temperature in a range of from 20 to 30° C., particularly preferably to room temperature.

The thermoplastic composition which has been obtained in process step iv) can furthermore be fed to a granulation before, during or also after carrying out process step v), but optionally also after process step iv) and without carrying out process step v).

Furthermore, in addition to the thermoplastic polymer (component a1) and the additive (component b1), the thermoplastic composition according to the invention can optionally also contain further additives (component c1). The further additives include in particular impact modifiers, filler materials, reinforcing agents, flame retardant compounds, heat and UV stabilizers, antioxidants, other processing auxiliaries, nucleating agents, dyestuffs and antidripping agents. Examples of suitable impact modifiers, filler materials, reinforcing agents and flame retardant compounds are to be found, inter alia, in US 2005/0234171 A1.

It is furthermore preferable in connection with the process according to the invention for components a1) to c1) to be mixed with one another in relative amounts such that the thermoplastic composition obtained by mixing components a1) to c1) contains a11) at least 40 wt. %, particularly preferably 50 to 99.8 wt. % and most preferably 60 to 99.6 wt. % of the thermoplastic polymer,
b11) 0.01 to 60 wt. %, particularly preferably 0.1 to 40 wt. % and most preferably 0.2 to 5 wt. % of the additive and
c11) 0 to 20 wt. %, particularly preferably 0.1 to 10 wt. % and most preferably 0.2 to 5 wt. % of the further additives in each case based on the total weight of the thermoplastic composition, wherein the sum of components a11) to c11) is 100 wt. %.

In another process embodiment according to the invention, it is preferable for components a12) to d12) to be mixed with one another in relative amounts such that the thermoplastic composition obtained by mixing components a12) to d12) contains a12) 1 to 69.99 wt. %, particularly preferably 1.5 to 49.8 wt. % and most preferably 2 to 19.6 wt. % of the thermoplastic polymer,
b12) 0.01 to 20 wt. %, particularly preferably 0.1 to 10 wt. % and most preferably 0.2 to 5 wt. % of the additive,
c12) at least 10 wt. %, preferably at least 20 wt. % and particularly preferably at least 30 wt. % of a biodegradable filler component and
d12) 0 to 20 wt. %, particularly preferably 0.1 to 10 wt. % and most preferably 0.2 to 5 wt. % of the further additives in each case based on the total weight of the thermoplastic composition, wherein the sum of components a12) to d12) is 100 wt. %. Possible biodegradable filler components are in principle all those which are known to the person skilled in the art and appear to be suitable. These include, in particular, mono- and polysugars, such as starch and starch derivatives, cellulose and cellulose derivatives, hemp, jute, bast, rush, reed, in particular reed flour, and other substances obtained from plants or a combination of at least two of these. In the context of this embodiment, it is furthermore preferable for the thermoplastic polymer to be based on a monomer which can be generated from renewable raw materials, such as lactic acid, to the extent of at least 10 wt. %, preferably to the extent of at least 50 wt. % and particularly preferably to the extent of at least 75 wt. %, in each case based on the thermoplastic polymer. This thermoplastic composition is suitable in particular for biodegradable non-returnable and disposable articles, such as utensils or cutlery.

It is moreover preferable according to the invention for a saturated, α-olefinic oligomer of at least one $C_6$-$C_{18}$-α-olefin to be employed in the course of the process according to the invention for the preparation of a thermoplastic composition in at most an amount such that the thermoplastic composition obtained by mixing components a1) to c1) contains less than 0.001 wt. %, particularly preferably less than 0.0005 wt. % and most preferably less than 0.0001 wt. % of the saturated, α-olefinic oligomer.

A contribution towards achieving the abovementioned objects is furthermore made by the thermoplastic composition obtainable by the process described above. Here and generally, it is preferable for the thermoplastic composition to have a yellow value of less than 6.64, preferably less than 6, particularly preferably less than 5 and furthermore preferably less than 4 and moreover preferably less than 3. The yellow value is often less than 2, or than 1. In the ideal case it is 0, but often more than 0.1 or 0.2.

The present invention also provides a process for the production of a shaped article, comprising the process steps:

I) provision of a thermoplastic composition obtainable by the process described above for the preparation of a thermoplastic composition;
II) heating of the thermoplastic composition to the glass transition temperature of the thermoplastic polymer or to a temperature above the glass transition temperature of the thermoplastic polymer;
III) production of a shaped article from the heated thermoplastic composition prepared in process step II).

In step I) of the process according to the invention for the production of a shaped article, a thermoplastic composition according to the invention is first provided, this provision preferably being carried out by a process according to the process described above for the preparation of a thermoplastic composition.

In process step II), the thermoplastic composition is then heated to the glass transition temperature of the thermoplastic polymer or to a temperature above the glass transition temperature of the thermoplastic polymer. In this connection, it is in turn preferable for the heating of the thermoplastic composition to be carried out to a temperature in a range of from 5° C. below the glass transition temperature ($T_g$) to 100° C. above the glass transition temperature of the thermoplastic polymer employed, particularly preferably to a temperature in a range of from 1° C. below the glass transition temperature ($T_g$) to 50° C. above the glass transition temperature of the thermoplastic polymer employed and most preferably to a temperature in a range of from 1° C. above the glass transition temperature ($T_g$) to 20° C. above the glass transition temperature of the thermoplastic polymer employed, here also, however the upper limit of the temperature range being essentially limited by the decomposition temperature of the thermoplastic polymer employed.

In principle, process steps I) and II) can be carried out simultaneously or in succession. It is appropriate to carry out process steps I) and II) simultaneously, for example, if the thermoplastic composition is prepared by means of a melt mixing process. Where appropriate, it may be advantageous here to convert the composition prepared by the melt mixing process directly into a shaped article. It is appropriate to carry out process steps I) and II) successively, for example, if the thermoplastic composition is prepared by means of a dry mixing process or if the thermoplastic composition is indeed prepared by means of a melt mixing process, but is not subjected to the formation of a shaped article directly after the preparation, but rather is first cooled according to process step v).

In process step III) of the process according to the invention for the production of a shaped article, a shaped article is produced from the heated thermoplastic composition prepared in process step II). Possible processes for the production of a shaped article are, in particular, injection moulding, extrusion moulding, compression moulding, layer moulding, laminating moulding, blow moulding, vacuum moulding and transfer moulding, injection moulding being particularly preferred.

Furthermore, in a preferred embodiment of the process according to the invention for the production of a thermoplastic shaped article, in at least one further process step IV) at least a part region of the shaped article obtained in process step III) serves as a shaped article blank and is reduced in its mass cross-section compared with process step III). The mass cross-section is the cross-section of a region of the shaped article made solidly from the thermoplastic moulding composition according to the invention. For example, in containers or vessels, the mass cross-section is the thickness of a wall of these containers or vessels. In the case of shaped articles which are rather thread- or strand-like in construction, the mass cross-section is the thickness of these threads or strands. In the case of rather planar structures, such as sheets, layers, webs, films or foils, the mass cross-section is the thickness of these planar structures. For the reduction in the mass cross-section, in principle all the methods known to the person skilled in the art and suitable for this are possible. These include, for example, stretching in one or two directions, drawing in one or two directions, centrifugation or blowing, each of which is preferably carried out at elevated temperatures at which the thermoplastic composition according to the invention is so soft or even liquid that stretching, drawing, centrifugation or blowing can be carried out. The part region in which the reduction in cross-section is effected preferably makes up at least 50% and particularly preferably at least 80% of the shaped article obtained in step III). Stretching or drawing are generally carried out if a fibre is to be obtained from the shaped article obtained in step III). For the production of films, on the one hand drawing or stretching in one or more dimensions can be carried out. Thus, the web running out of an extruder can be drawn on to a roll at a higher speed compared with the exit speed from the extruder. On the other hand, if a container or vessel is to be obtained, apart from stretching, drawing and centrifugation, blowing is chiefly employed in step IV). In this, the reduction in mass cross-section is effected by applying a gas pressure. The gas pressure is generally chosen such that the thermoplastic composition, which is usually heated at least to the glass transition temperature, of the shaped article obtained in step III) can be extended. The extending is as a rule limited by using a mould having the final shape of the shaped article. In addition to containers, such as freezer boxes, dishes and packaging for foodstuffs, such as fruit, vegetables or meat, as well as medicaments as tablets, capsules, suppositories or powders, vessels for liquids can also be produced in this way. As well as for liquids of the cosmetics or pharmaceuticals industry, these vessels for liquids can also be used in the foodstuffs industry, preferably in the drinks industry, as reusable vessels, such as PET or PLA bottles. It is furthermore possible for two or more of process steps I) to IV) to be supplemented by further process steps and/or to at least overlap in time. This applies in particular to process steps III) and IV).

In addition to bottles, other shaped articles can furthermore also be produced according to the invention. These include disposable and reusable vessels, such as plates, dishes, pots or beakers, and cutlery, such as knives, forks or spoons. The biodegradable thermoplastic compositions according to the invention are particularly suitable for these uses.

The present invention also provides a process for the production of a packed product, comprising the process steps:

a) provision of a product and a shaped article, in particular a film, the shaped article being obtainable by the process described above;
b) at least partial surrounding of the product with the shaped article.

The product provided in process step a) is preferably a pharmaceutical, a body care composition, an agricultural auxiliary substance, an adhesive, a building material, a dyestuff or a foodstuff.

The at least partial surrounding of the product can be carried out, for example, by the process described in DE-A-103 56 769.

The present invention also provides a process for the production of an at least partly coated object, comprising the process steps:
  a4) provision of a coating composition comprising at least 10 wt. %, based on the coating composition, of an ester or a thermoplastic composition obtainable by the particular process described above, and of a solid substrate;
  b4) mixing of the coating composition and the substrate, the coating composition being at least partly liquid.

The production of the at least partly coated object with the coating composition can be carried out, for example, by a procedure in which the coating composition and the object to be coated are mixed with one another in suitable mixing devices, the Patterson-Kelly mixer, DRAIS turbulence mixer, Lödige mixer, Ruberg mixer, screw mixers, plate mixers and fluidized bed mixers being possible in particular as mixing devices. Should the coating composition not be liquid under the mixing conditions, this component is to be heated to a temperature above the melting temperature of the coating composition before or during the mixing with the object to be coated. In addition to the use of the mixing devices described above, the production of the at least partly coated object can also be carried out by a procedure in which, for example, the object to be coated is initially introduced into a fluidized bed mixer and the coating composition is sprayed in liquid form on to the object to be coated.

The present invention also provides a further processing product comprising an ester which is obtainable by reaction of a carboxylic acid component with an alcohol component which is capable of reacting with the carboxylic acid component to form an ester, and at least one functional component chosen from the group consisting of thermoplastic polymer, enzyme, curing agent of an adhesive, paraffin, oil, colouring agent, hair or skin care substance, polymer dispersion, lime mud, lubricant or emulsifier, or a combination of two or more of these.

The present invention also provides the use of an ester which is obtainable by reaction of a carboxylic acid component with an alcohol component which is capable of reacting with the carboxylic acid component to form an ester, as an additive in a composition which is chosen from the group consisting of: thermoplastic composition, detergent, adhesive, defoamer, lubricant formulation, lacquer, paint, cosmetic formulation, soil compacting agent, drilling mud, hydraulic oil or dispersion.

The present invention also provides the use of an ester which is obtainable by reaction of a carboxylic acid component with an alcohol component which is capable of reacting with the carboxylic acid component to form an ester, as an additive in a composition comprising as a functional component
  α) a thermoplastic polymer, the composition being a thermoplastic composition;
  β) an enzyme, the composition being a detergent;

γ) a curing agent of an adhesive, the composition being an adhesive;

δ) a paraffin, the composition being a defoamer;

ε) an oil, the composition being a lubricant formulation;

ζ) colouring agent, the composition being a lacquer or a paint; or

η) a hair or skin care substance, the composition being a cosmetic formulation,

θ) a polymer dispersion, the composition being a soil compacting agent,

ι) a lime mud, the composition being a drilling mud,

κ) a lubricant, the composition being a hydraulic oil,

λ) an emulsifier, the composition being a thermoplastic composition or a dispersion, wherein the ester has preferably been obtained by the process according to the invention described above for the preparation of an ester comprising process steps i., ii. and optionally iii.

Preferably, the additive is employed in an amount in a range of from 0.001 to 40 wt. %, particularly preferably in a range of from 0.01 to 20, very particularly preferably from 0.1 to 10 wt. % and particularly preferably in a range of from 0.5, 1 or 2 to 5, 6, 7 or 8 wt. %, based on the composition.

The invention is now explained in more detail with the aid of non-limiting examples.

Measurement Methods

Unless expressly stated otherwise, all the measurements are carried out in accordance with the relevant ISO standards. Unless specified otherwise there, a temperature of 23° C., an atmospheric pressure of 1 bar and a relative atmospheric humidity of 50% was chosen.

Composition of a Mixture of Several Carboxylic Acid Components

Mixtures of several carboxylic acid components such as are present, for example, in technical grade oleic acid can be determined by means of gas chromatography (GC) or high pressure liquid chromatography (HPLC). The weight contents are stated in wt. %, based on the total weight of the sample supplied.

Determination of the Yellow Value

As a measure of the yellow shading/yellowing, the yellow value is determined in accordance with DIN 5033 as the b* value of a sample of the composition to be analysed according to the L*,a*,b* colour system.

Thermal Analysis

The thermal parameters were determined by means of DSC (dynamic heat flow differential calorimetry) on a Mettler Toledo DSC 821. The amount weighed out was 20-25 mg in an open crucible. After closing the crucible, the samples prepared in this way were measured over a temperature range of from −100 to +120° C. at a heating rate of 20 K/min against an empty, likewise closed crucible. The sample was kept at +120° C. for 60 seconds and then cooled with the highest possible cooling rate of the apparatus, but at least 15 K/min, to the abovementioned minimum temperature, and kept at this for 2 min before the heating and cooling operation was repeated.

The glass transition temperature and the melting temperature are determined in accordance with DIN 53765.

The degree of crystallization can be determined with the aid of the formula: $K=\Delta H_m/\Delta H_m^\circ \times 100\%$, where K represents the degree of crystallization, $\Delta H_m$ represents the enthalpy of fusion of the sample and $\Delta H_m^\circ$ represents the enthalpy of fusions of the material at a crystallinity of 100%.

The $\Delta H_m^\circ$ values can be found by the person skilled in the art in the tabular works known to him, e.g. J. Brandrup et al., "*Polymer Handbook*", 4th ed., John Wiley & Sons.

Further Methods

The following characteristic values are determined in accordance with published standards:

| Characteristic value | Standard | Comments |
|---|---|---|
| BET surface area | DIN 66131 | with nitrogen |
| Hydroxyl number (OHN) | DIN 53240 | |
| Acid number (AN) | DIN EN ISO 3682 | |
| Saponification number (SN) | DIN 53401 | |
| Pour point | DIN ISO 3016 | |
| Cloud point | DIN ISO 3015 | |
| Glass transition temperature ($T_g$), melting point ($T_m$) | DIN 53765 | see above |
| Density | DIN 51757 | at 20° C. |
| Viscosity | DIN 53015 | at 20° C. |
| Gardner colour number | DIN EN ISO 4630-1 | |
| Thickness of the multifilament [μm] | DIN 53855 Part 1 | |
| Particle size by means of laser diffractometry | ISO13320-1 | on Coulter 230 LS |
| Water content | DIN 51777 | Karl-Fischer method |

EXAMPLES

Unless noted otherwise, the raw materials, obtainable under the trade names given, are obtainable from Cognis Oleochemicals Deutschland GmbH, Düsseldorf, or from Sigma-Aldrich Chemie GmbH, Steinheim.

Example 1

Preparation of Carboxylic Acid N-Alkyl Esters

Alcohol and carboxylic acid were initially introduced into a flask with a blade stirrer and distillation bridge in the ratio of substance amounts shown in Table 1, and a catalyst system was added. The reaction mixture was heated from $T_s$ to $T_c$ in the course of $t_r$. Thereafter, an reactant-specific vacuum was applied for a further time $t_v$ and the excess reactants were distilled off up to a temperature of a maximum of 220° C. The mixture was cooled to 90° C. and filtered.

The yield was determined with respect to the carboxylic acid weighed out. The experimental data, such as weight of alcohol, carboxylic acid and catalyst system, and also the yield, colour number and acid number, are summarized in Table 1. The temperature data relate to the temperature of the reaction vessel.

TABLE 1

| Example no. | Catalyst system | Weight content of catalyst/ (carboxylic acid + alcohol) [wt. %] | Carboxylic acid | Alcohol | Ratio of substance amounts carboxylic acid:alcohol [$n_{CA}$:$n_{ROH}$] | $T_s$[1] [° C.] | $T_e$[2] [° C.] | $t_r$[3] [h] | $t_v$[4] [h] | Yield [wt. %] | Gardner colour number | Acid number |
|---|---|---|---|---|---|---|---|---|---|---|---|---|
| 1 (comp.) | $H_2SO_4$ | 0.1 | oleic acid | n-octanol | 1.2:1 | 150 | 180 | 3 | 4 | 92 | 10 | 1.0 |

TABLE 1-continued

| Example no. | Catalyst system | Weight content of catalyst/ (carboxylic acid + alcohol) [wt. %] | Carboxylic acid | Alcohol | Ratio of substance amounts carboxylic acid:alcohol [$n_{CA}$:$n_{ROH}$] | $T_s$[1] [°C.] | $T_e$[2] [°C.] | $t_r$[3] [h] | $t_v$[4] [h] | Yield [wt. %] | Gardner colour number | Acid number |
|---|---|---|---|---|---|---|---|---|---|---|---|---|
| 2 (comp.) | SnOx$_2$ | 0.052 | oleic acid | n-octanol | 1.6:1 | 150 | 180 | 3 | 4 | 10 | 7 | 1.0 |
| 3 | SnOx$_2$/H$_2$SO$_4$ | 0.05/0.1 | oleic acid | n-octanol | 1.2:1 | 150 | 180 | 3 | 4 | 91 | 5 | 1.0 |
| 4 | SnOx$_2$/PTSC | 0.05/0.1 | oleic acid | n-octanol | 1.2:1 | 150 | 180 | 3 | 4 | 92 | 6 | 1.0 |
| 5 | SnOx$_2$/H$_2$SO$_4$/ H$_3$PO$_2$ | 0.05/0.1/0.03 | oleic acid | n-octanol | 1.2:1 | 150 | 180 | 3 | 4 | 91 | 4 | 1.0 |
| 6 (comp.) | H$_2$SO$_4$ | 0.1 | stearic acid | n-butanol: | 1.2:1 | 150 | 160 | 6 | 3 | 90 | 6 | 1.0 |
| 7 (comp.) | SnOx$_2$ | 0.05 | stearic acid | n-butanol: | 1.2:1 | 150 | 160 | 6 | 3 | —[5] | —[5] | —[5] |
| 8 | SnOx$_2$/H$_2$SO$_4$ | 0.05/0.1 | stearic acid | n-butanol: | 1.2:1 | 150 | 160 | 6 | 3 | 91 | 2 | 0.7 |
| 9 | SnOx$_2$/PTSC | 0.05/0.1 | stearic acid | n-butanol: | 1.2:1 | 150 | 160 | 6 | 3 | 90 | 1 | 0.5 |
| 10 | SnOx$_2$/PTSC/ H$_3$PO$_2$ | 0.05/0.1/0.03 | stearic acid | n-butanol: | 1.2:1 | 150 | 160 | 15 | 5 | 93 | 1 | 0.6 |

[1]Temperature at the start of the reaction;
[2]Temperature at the end of the reaction;
[3]Duration of the reaction;
[4]Duration of the vacuum treatment at $T_e$.
H$_2$SO$_4$: sulphuric acid, 98%;
SnOx$_2$: tin oxalate;
PTSC: p-toluenesulphonic acid;
H$_3$PO$_2$: hypophosphorous acid, 50%;
[5]no reaction.

It can be seen from Table 1 that the use of the catalyst mixtures of Ex. 3-5 and 8-10 leads to improved values for the colour number and a comparatively high yield.

Example 11

Preparation of a Thermoplastic Composition 6 kg of polyethylene terephthalate (PET SP04 from Catalana de Polimers, Barcelona) was introduced into a 15 kg Henschel mixer. The mixing wall temperature was 40° C. 0.5 wt. % of the ester prepared in Example 10 was furthermore added as a mould release agent. The material was then granulated on a granulator (ZSK 26Mcc) with a stuffing screw.

Example 12

Production of a Shaped Article

For production of shaped articles from the thermoplastic composition prepared in Example 11, a fully hydraulic injection moulding machine with a hydraulic closing unit of the Battenfeld HM800/210 type was employed. The maximum closing force is 800 kN, the screw diameter is 25 mm. A mould with a conically tapering, rectangular core was used at the test mould. For determination of the demoulding force, a load cell with a maximum measuring range of 2 kN was attached to the ejector rod. The moulding composition was predried at about 225° C. for about 4 hours. Significantly improved demoulding was observed with the thermoplastic composition according to the invention compared with an additive-free moulding composition.

Example 13

Preparation of a Detergent 0.2 wt. % of zinc ricinoleate (Tego® Sorb Conc 50 from Goldschmidt), 1 wt. % of sodium citrate, 0.1 wt. % of the ester obtained in Example 5, as a defoamer, 1 wt. % of boric acid, 7.5 wt. % of glycerol, 1 wt. % of ethanol, 4 wt. % of C$_{12}$-C$_{16}$ alkyl glycoside, 8 wt. % of soap, 8 wt. % of C$_{12}$-C$_{14}$-fatty alcohol+1.3 EO sulphate sodium salt, 1 wt. % of Acusol 120 (15% strength; methacrylic acid (stearyl alcohol-20-EO) ester/acrylic acid copolymer from Rohm & Haas), 0.5 wt. % of Dequest 2066, amylase, protease, and water were mixed to give a detergent.

Example 14

Preparation of an Adhesive

A high molecular weight diisocyanate was prepared from a polypropylene glycol of $M_n$=880 g/mol and diphenylmethane-diisocyanate in accordance with the teaching of DE-A-199 57 351, and the monomeric MDI was then removed from this until a residual monomer content of 0.1% resulted. A hot-melt adhesive was prepared from 100 parts of a polyol mixture for a standard polyurethane hot-melt adhesive (QR 6202, Henkel) having an average OH number of 32.5 and 76.5 parts of the above-mentioned high molecular weight diisocyanate. 5 wt. % of the ester prepared in Example 5 was additionally added.

Example 15

Preparation of a Defoamer 4.0 wt. % of paraffin having a solidification point according to DIN ISO 2207 of 45° C., a liquid content at 40° C. of about 66 wt. % and a liquid content at 60° C. of about 96 wt. %, 1,2 wt. % of bisamide, 3 wt. % of sodium carbonate, 58.7 wt. % of sodium sulphate, 21.4 wt. % of sodium silicate, 2.1 wt. % of cellulose ether, 4.8 wt. % of the ester obtained in Example 5 and water are mixed to form an aqueous slurry, which was spray dried with superheated steam by the process of the European patent specification EP 625 922.

Example 16

Preparation of a Defoamer II 1.2 wt. % of bisamide, 3 wt. % of sodium carbonate, 58.7 wt. % of sodium sulphate, 21.4 wt. % of sodium silicate, 2.1 wt. % of cellulose ether, 8.8 wt. % of the ester obtained in Example 5 and water are mixed to form an aqueous slurry, which was spray dried with superheated steam by the process of the European patent specification EP-A-0 625 922.

Example 17

Preparation of a Textile Auxiliary 5 g of the polymer emulsion prepared according to Example 1b of DE-A-39 39 549 were added to 995 g of a textile lubricant comprising 84.5 wt. % of n-butyl stearate from Example 10, 5 wt. % of oleyl/cetyl alcohol 5 mol EO, 2.2 wt. % of coconut fatty acid monoethanolamide 4 mol EO, 0.8 wt. % of oleic acid, 6 wt. % of secondary fatty alcohol 7 mol EO (Tergitol 15S7, manufacturer: Union Carbide) and 1.5 wt. % of water at 20° C., while stirring (maximum stirring speed of an overhead stirrer with a propeller stirrer). After 30 seconds, the polymer emulsion had become uniformly distributed and a clear solution was formed. Thereafter, the stirring speed was reduced as far as possible and the textile lubricant was heated to 60° C. to accelerate dissolving of the polymer particles.

Example 18

Preparation of a Lacquer 736 g of demineralized water, 4 g of a 70 wt. % solution of sebacic acid dioctyl ester in $C_{12}H_{26}$ (isomer mixture), 10 g of sodium nitrobenzenesulphonate, 5 g of the tetrasodium salt of ethylenediaminetetraacetic acid, 100 g of urea, 25 g of sodium bicarbonate, 100 g of D-I.1 and 20 g of Fluorescent Brightener C.I. 230 were mixed. 5 g of the oleic acid n-octyl ester obtained in Example 5 were added as a defoamer and the mixture was stirred with a high-speed stirrer at 2,000 rpm for 60 seconds.

Example 19

Preparation of a Cosmetic Formulation

O/W emulsions were prepared, the oil phases of which had the following composition:
5.0 g of the compounds characterized by the formula (I) in EP-A-1 485 061, in which R' represents methyl and R in each case represents a butyloctanoyl radical ($C_{12}$),
5.0 g of the emulsifier dioctyl ether (Cetiol OE, Cognis),
0.6 g of the emulsifier cetyl stearyl alcohol+20 EO (Eumulgin B2, Cognis),
0.1 g of creatine.
5 wt. % of the ester obtained in Example 5 was added to the composition obtained in this way.

Example 20

Preparation of a Drilling Mud

A conventional lime mud was prepared from 7.6 g of prehydrated bentonite, 1.15 g of ferrochrome lignosulphonate, 2.3 g of slaked lime, 0.38 g of starch and 0.76 g of NaOH. 5 wt. % of the ester obtained in Example 5 was additionally added to this lime mud.

Example 21

Preparation of a Soil Compacting Agent

To a commercially available polyvinyl acetate dispersion (approx. 50 wt. % of polyvinyl acetate, obtainable from Henkel KGaA, Düsseldorf), 10 wt. %, based on the aqueous dispersion, of
a) oleic acid triglyceride,
b) oleic acid n-octyl ester from Example 5, or
c) stearic acid (n-butyl ester) from Example 10, is added.
As experiment d), a film was obtained from the untreated dispersion, which serves as a reference.
Films with an average thickness of (400±30) µm are produced from these dispersions a) to c) by dipcoating on rotating Teflon discs of 10 cm diameter.
These films are evaluated with respect to flexibility, water-solubility and cohesion. After 21 days, they were tested for stability and homogeneity.
In comparison with the reference experiment d), all three dispersions a) to c) show a significantly improved flexibility of the films after three weeks. Films a) to c) moreover show an extremely high cohesion compared with d) immediately after film formation and in particular also after three weeks, so that they tear only when a high force is applied.
Field experiments in which aa) layers of sand, bb) potting compost and cc) sandy loess were treated with dispersions a) to d) and exposed to weathering in the Düsseldorf, Germany region for 3 weeks proved to be highly compacted in the case of a) to c) compared with the reference d).

List of Reference Symbols on FIG. 1
Reaction region 110
Reactor 111
Heating jacket 112
Baffle 113
Stirrer shaft 211
Stirrer blade 212
Transmission 213
Motor 214
Working up unit 311
External heat exchanger 411
Feed line 511
Reactant reservoir 512
Delivery pump 911
Distributing device 912
Circulation line 921
Return line, flange 922
Feed of process components 932
Vapours line 941
Heat exchanger 942
Pressure reducing unit 945
Separator with interfacial layer 946
Receiver 947
Return line 948
Filling level line F

The invention claimed is:
1. A process for the preparation of an ester, at least based on
a. at least one alcohol component,
b. at least one carboxylic acid component,
c. optionally further additives,
d. at least two different catalysts, and
e. max 20 wt. % of a solvent;
as process components, comprising, in a reactor, the process steps:
i. provision of the process components, ii. reaction of the process components to give an ester A,
iii. optionally after-treatment of the ester A,
wherein at least in each case one of the at least two different catalysts is an electron donor and a further catalyst of the at least two different catalysts is a sulphur-containing proton donor;
wherein
   aa. sulphuric acid, or
   bb. an aliphatic, cycloaliphatic or aromatic $C_1$ to $C_{10}$-sulphuric acid, or a combination of two or more of these, is chosen as the sulphur-containing proton donor; and
wherein a metal, a metal compound, or a reducing acid, or a combination of two or more of these is employed as the electron donor.

2. The process according to claim 1, wherein the carboxylic acid component contains non-metal atoms chosen from the group of carbon, oxygen, nitrogen or hydrogen.

3. The process according to claim 1, wherein the carboxylic acid component comprises more than 5 carbon atoms.

4. The process according to claim 1,
   wherein the amount of electron donor, based on the total amount of catalysts, is more than 12.5 wt. %.

5. The process according to claim 1, wherein
   aa) a metal chosen from the group consisting of: titanium, tin, zirconium, in particular tin, or
   bb) a metal compound chosen from the group consisting of: tetralkyl titanate, organotitanium complex, titanium salt, tin alkanoate, tin tetraalcoholate, organotin complex, zirconium salt, organozirconium complex, in particular tin alkanoate and organotin complex, such as a tin octoate, tin oxalate or dibutyltin dilaurate, or
   cc) a reducing acid chosen from the group consisting of: sulphurous acid, hypophosphorous acid, phosphorous acid,
or two or more of these, is chosen as the electron donor.

6. The process according to claim 1, wherein the reaction is carried out at a temperature in a range of from 80 to 185° C., in particular from 100 to 185° C.

7. The process according to claim 1, wherein the reaction is carried out under a pressure in a range of from 2 to 800 mbar.

8. The process according to claim 1, wherein the weight content of catalyst is in a range of from 0.01 wt. % to 0.5 wt. %, based on the total amount of process components weighed out.

9. The process according to claim 1, wherein a catalyst mixture of
   5 to 50 wt. % of tin oxalate,
   12.5 to 50 wt. % of hypophosphorous acid, and
   30 to 90 wt. % of p-toluenesulphonic acid,
which can in each case be chosen independently of each other, is employed as the catalysts,
wherein
the sum of all the wt. % is 100.

10. The process according to claim 1, wherein no steam distillation is carried out as an after-treatment step.

11. The process according to claim 1, wherein an alcohol component with one or more hydroxyl groups is chosen as the alcohol component.

12. The process according to claim 1, wherein a partial ester is prepared as the ester, wherein either
   I. an alcohol component with two or more hydroxyl groups is reacted with a carboxylic group,
   II. a carboxylic component with two or more carboxyl groups is reacted with an alcohol component with one hydroxyl group, or
   III. a carboxylic acid component with two or more carboxyl groups is reacted with an alcohol component with two or more hydroxyl groups.

13. The process according to claim 1, wherein the carboxylic acid component is chosen from the group consisting of octanoic acid, i-octanoic acid, nonanoic acid, i-nonanoic acid, decanoic acid, i-decanoic acid, sebacic acid, palmitic acid, stearic acid, oleic acid, azelaic acid, pelargonic acid, behenic acid, trimellitic acid, adipic acid, erucic acid, HOOC—$C_{36}H_{72}$—COOH, phthalic anhydride or a mixture of two or more of these.

14. The process according to claim 1, wherein the alcohol component is chosen from the group consisting of glycerol, oligoglycerols, pentaerythritol, pentaerythritol dimer, n-butanol, i-butanol, n-propanol, i-propanol, 2,2-dimethylpropanol, 2-ethylhexanol, n-octanol, i-tridecanol, cetyl alcohol, stearyl alcohol, ethylene glycol, diethylene glycol, butyl glycol, dibutyl glycol, tributyl glycol, 2-propylheptanol, polyethylene glycol or a mixture of two or more of these.

15. The process according to claim 1, wherein the ester has between 1 and 6 ester groups.

* * * * *